(12) United States Patent
Desmarais

(10) Patent No.: US 10,632,301 B2
(45) Date of Patent: Apr. 28, 2020

(54) MEDICAL DEVICE CONNECTOR FOR COUPLING ELECTRODES

(71) Applicant: ZOLL Medical Corporation, Chelmsford, MA (US)

(72) Inventor: Christopher Joseph Desmarais, Acushnet, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

(21) Appl. No.: 15/282,073

(22) Filed: Sep. 30, 2016

(65) Prior Publication Data
US 2018/0093090 A1    Apr. 5, 2018

(51) Int. Cl.
*A61N 1/04* (2006.01)
*A61N 1/39* (2006.01)
*A61B 5/046* (2006.01)
*A61B 5/0408* (2006.01)

(52) U.S. Cl.
CPC .......... *A61N 1/048* (2013.01); *A61N 1/046* (2013.01); *A61B 5/046* (2013.01); *A61B 5/04087* (2013.01); *A61B 2562/226* (2013.01); *A61N 1/0492* (2013.01); *A61N 1/3925* (2013.01)

(58) Field of Classification Search
CPC .......... A61N 1/048; A61N 1/375; A61N 1/08; A61N 1/0484; A61N 1/362; A61N 1/02; A61N 1/044; A61N 1/22; A61N 1/321; A61N 1/36; A61N 1/3752; A61N 1/3756; A61B 2562/0209; A61B 2562/227; A61B 5/04085; A61B 5/0416; A61B 2560/0412; A61B 2562/164; A61B 5/6804; A61B 2562/14; A61B 5/0004; A61B 5/0006; A61B 5/6831

See application file for complete search history.

(56) References Cited

U.S. PATENT DOCUMENTS

| | | | |
|---|---|---|---|
| 4,928,690 A | 5/1990 | Heilman et al. | |
| 5,078,134 A | 1/1992 | Heilman et al. | |
| 5,741,306 A | 4/1998 | Glegyak et al. | |
| 5,944,669 A | 8/1999 | Kaib | |
| 6,065,154 A | 5/2000 | Hulings et al. | |

(Continued)

OTHER PUBLICATIONS

ZOLL Wearable Defibrillator Model HWD 1000 Operator's Manual, 5 pages, PN 20B0054-A01 Rev FI, ZOLL, Pittsburgh, Pennsylvania.

*Primary Examiner* — Deborah L Malamud
(74) *Attorney, Agent, or Firm* — ZOLL Medical Corporation

(57) ABSTRACT

An electrode assembly for patient monitoring and treatment can include an electrode configured to be worn by a patient to provide at least one of monitoring a cardiac function of the patient and delivering a treatment for cardiac arrhythmia to the patient; and a first connector connected to and in communication with the electrode, the first connector including a male connection portion. The male connection portion is configured to engage a second connector to form a mating engagement between the first connector and the second connector. The male connection portion includes at least one orientation aligning feature configured to engage the male connection portion of the first connector with the second connector in a fixed orientation with respect to the second connector to form the mating engagement. The first connector has a flattened profile.

10 Claims, 15 Drawing Sheets

(56) References Cited

U.S. PATENT DOCUMENTS

| | | |
|---|---|---|
| 6,253,099 B1 | 6/2001 | Oskin et al. |
| 6,280,461 B1 | 8/2001 | Glegyak et al. |
| 6,681,003 B2 | 1/2004 | Linder et al. |
| 6,961,611 B2 | 11/2005 | Dupelle |
| 7,016,726 B1 * | 3/2006 | Picardo .................... A61N 1/08 239/449 |
| 8,172,459 B2 * | 5/2012 | Abreu .................. A61B 5/0002 374/208 |
| 8,271,082 B2 | 9/2012 | Donnelly et al. |
| 8,369,944 B2 | 2/2013 | Macho et al. |
| 9,028,407 B1 * | 5/2015 | Bennett-Guerrero ........................ A61B 5/1121 600/301 |
| 2013/0325096 A1 | 12/2013 | Dupelle et al. |

\* cited by examiner

MEDICAL DEVICE CONNECTOR FOR COUPLING ELECTRODES

TECHNICAL FIELD

The present disclosure relates to a connector assembly for connecting a cardiac monitoring and therapeutic medical device, such as a wearable defibrillator, with one or more cardiac monitoring and/or therapeutic electrodes attached to a patient.

BACKGROUND

One of the most deadly forms of heart arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death may result in minutes if normal heart contractions are not restored. Although frequently not noticeable to the victim, ventricular fibrillation is often preceded by ventricular tachycardia, which is a regular but fast rhythm of the heart. Because the victim has no noticeable warning of the impending fibrillation, death often occurs before the necessary medical assistance can arrive.

Because time delays in applying the corrective electrical treatment may result in death, pacemakers and defibrillators have significantly improved the ability to treat these otherwise life-threatening conditions. Normal heart function often can be restored to a person suffering ventricular fibrillation or ventricular tachycardia by a procedure known as cardioversion, the synchronized application of electrical therapy to the heart muscle. Pacemakers and defibrillators that apply corrective electrical pulses externally to the patient's chest wall also are used to correct such life-threatening arrhythmias, but suffer from a drawback insofar as it may not be possible to apply the device in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. However, patients that have recently had a heart attack or are awaiting such an implantable device may be kept in a hospital where corrective electrical therapy is generally close at hand. Long-term hospitalization is frequently impractical due to its high cost, or due to the need for patients to engage in normal daily activities.

Wearable defibrillators have been developed for patients that have recently experienced cardiac arrest, that are susceptible to heart arrhythmias and are at temporary risk of sudden death, and that are awaiting an implantable device. However, some wearable defibrillators may incorporate direct connections between the wearable defibrillator and the electrodes worn by the patient, which can make it difficult to efficiently replace the electrode, or may incorporate large and bulky connectors that are difficult to manipulate and interfere with the patient's movement.

Accordingly, a need exists for an improved connector assembly for connecting a cardiac monitoring and/or treatment device such as a wearable defibrillator to one or more cardiac monitoring and/or therapeutic electrodes worn by the patient.

SUMMARY

Non-limiting examples of embodiments will now be described.

In an example, an electrode assembly for patient monitoring and treatment is provided. The electrode assembly can comprise: an electrode configured to be worn by a patient to provide extended and continuous monitoring of a cardiac function of the patient and delivery of a treatment for cardiac arrhythmia to the patient; and a first connector connected to the electrode, the first connector comprising a male connection portion and at least one electrical contact disposed in the male connection portion. The electrical contact is configured to engage a corresponding electrical contact in a second connector for facilitating the extended and continuous monitoring of a cardiac function of the patient and delivery of a treatment for cardiac arrhythmia to the patient, the second connector comprising a female connection portion. The male connection portion and the female connection portion are configured to form a mating engagement between the first connector and the second connector. The male connection portion comprises at least one orientation aligning feature configured to engage the male connection portion of the first connector with the female connection portion of the second connector in a fixed orientation with respect to the second connector to form the mating engagement such that the electrical contacts engage with each other. The first connector has a flattened profile.

The at least one electrical contact of the first connector can be configured to transmit a continuous cardiac monitoring signal and a cardiac treatment signal.

The first connector can further comprise a plurality of electrical contacts disposed in the male connection portion and configured to engage corresponding electrical contacts in the second connector when the mating engagement is formed. The plurality of electrical contacts comprises at least one contact configured to transmit a continuous cardiac monitoring signal and at least one contact configured to transmit a cardiac treatment signal.

The plurality of electrical contacts can further comprise at least one ground contact.

The male connection portion of the first connector can comprise at least two locking features. The at least two locking features are configured to engage retaining features on the second connector to retain the first connector in the mating engagement. The at least two locking features are configured to be engaged simultaneously by a release mechanism on the second connector to release the first connector from the mating engagement.

The electrode assembly can further comprise the second connector, the second connector being connected to a device for ambulatory cardiac monitoring and treatment. The female connection portion is configured to be engaged by the male connection portion of the first connector to form the mating engagement.

The male connection portion of the first connector can comprise at least two locking features. The female connection portion of the second connector can comprise at least two retaining features configured to be engaged by the locking features on the male connection portion to retain the first connector and the second connector in the mating engagement. The second connector can further comprise a release mechanism configured to be actuated to simultaneously engage the at least two locking features to release the first connector and the second connector from the mating engagement.

The at least two locking features of the male connection portion can comprise flexible locking tabs disposed on the male connection portion. The at least two retaining features of the female connection portion can comprise apertures extending at least partially through the female connection portion from an interior toward a respective one of the first and second sides of the second connector. The release mechanism can comprise at least two buttons disposed in a resiliently flexible material on each of the first and second sides of the second connector, each of the buttons comprising a depending portion that extends into a respective aperture and is configured to contact a respective locking tab on the male connection portion when the button is depressed to cause the respective locking tab to disengage from the respective aperture.

In another example, an electrode assembly for patient monitoring and treatment is provided. The electrode assembly can comprise: an electrode configured to be worn by a patient to provide extended and continuous monitoring of a cardiac function of the patient and delivery of a treatment for cardiac arrhythmia to the patient; and a first connector connected to and in communication with the electrode. The first connector comprises a male connection portion. The male connection portion is configured to engage a second connector in a mating engagement. The male connection portion of the first connector comprises at least two locking features. The at least two locking features are configured to engage retaining features on the second connector to retain the first connector in the mating engagement. The at least two locking features are configured to be engaged simultaneously by a release mechanism on the second connector to release the first connector from the mating engagement.

The first connector can further comprise at least one electrical contact disposed in the male connection portion and configured to engage a corresponding electrical contact in the second connector when the mating engagement is formed. The at least one electrical contact is configured to transmit a continuous cardiac monitoring signal and a cardiac treatment signal.

The first connector can further comprise a plurality of electrical contacts disposed in the male connection portion and configured to engage corresponding electrical contacts in the second connector when the mating engagement is formed. The plurality of electrical contacts comprises at least one contact configured to transmit a continuous cardiac monitoring signal and at least one contact configured to transmit a cardiac treatment signal.

The plurality of electrical contacts can further comprise at least one ground contact.

The electrode assembly can further comprise the second connector, the second connector being connected to a device for ambulatory cardiac monitoring and treatment and comprising a female connection portion. The female connection portion is configured to be engaged by the male connection portion of the first connector to form the mating engagement.

The first connector and the second connector can comprise corresponding orientation aligning features configured to engage the first connector and the second connector with each other in a fixed orientation with respect to each other to form the mating engagement.

The female connection portion of the second connector can comprise at least two of the retaining features configured to be engaged by the at least two locking features on the male connection portion to retain the first connector and the second connector in the mating engagement. The second connector can further comprise the release mechanism configured to be actuated to simultaneously engage the at least two locking features to release the first connector and the second connector from the mating engagement.

The at least two locking features of the male connection portion can comprise flexible locking tabs disposed on the male connection portion. The at least two retaining features of the female connection portion can comprise apertures extending at least partially through the female connection portion from an interior toward a respective one of the first and second sides of the second connector. The release mechanism can comprise at least two buttons disposed in a resiliently flexible material on each of the first and second sides of the second connector, each of the buttons comprising a depending portion that extends into a respective aperture and is configured to contact a respective locking tab on the male connection portion when the button is depressed to cause the respective locking tab to disengage from the respective aperture.

The first connector can have a flattened profile.

In another example, an electrode assembly for patient monitoring and treatment is provided. The electrode assembly can comprise: an electrode configured to be worn by a patient to provide extended and continuous monitoring of a cardiac function of the patient and delivery of a treatment for cardiac arrhythmia to the patient; and a first connector connected to the electrode, the first connector comprising a male connection portion. The male connection portion is configured to engage a second connector to form a mating engagement between the first connector and the second connector. The male connection portion comprises at least one orientation aligning feature configured to engage the male connection portion of the first connector with the second connector in a fixed orientation with respect to the second connector to form the mating engagement. The first connector has a flattened profile. The male connection portion of the first connector comprises at least two locking features. The at least two locking features are configured to engage retaining features on the second connector to retain the first connector in the mating engagement. The at least two locking features are configured to be engaged simultaneously by a release mechanism on the second connector to release the first connector from the mating engagement.

In another example, a patient monitoring and treatment system is provided. The system can comprise: an ambulatory cardiac monitoring and treatment device; a first electrode configured to be worn by a patient to provide at least one of monitoring a cardiac function of the patient and delivering a treatment for cardiac arrhythmia to the patient; a second electrode configured to be worn by a patient to provide at least one of monitoring a cardiac function of the patient and delivering a treatment for cardiac arrhythmia to the patient; a first connector connected to and in communication with the first electrode, the first connector comprising a male connection portion; a second connector connected to and in communication with the monitoring and treatment device, the second connector comprising a female connection portion; a third connector connected to and in communication with the second electrode, the third electrode comprising a male connection portion; and a fourth connector connected to and in communication with the monitoring and treatment device, the fourth connector comprising a female connection portion. The male connection portion of the first connector is configured to engage the female connection portion of the second connector to form a mating engagement between the first connector and the second connector. The first connector and the second connector are configured to transmit at least one of a patient monitoring signal and a patient treatment signal between the first electrode and the monitoring and treatment device when the mating engagement is formed. The male connection portion of the third connection portion is configured to engage the female connection portion of the fourth connector to form a mating engagement between the third connector and the fourth connector. The third connector and the fourth connector are configured to transmit at least one of a patient monitoring signal and a patient treatment signal between the second electrode and the monitoring and treatment device when the mating engagement is formed.

The first electrode is configured to be worn by the patient at the patient's sternum.

The second electrode is configured to be worn by the patient at the patient's apex.

The male connection portion of the first connector and the female connection portion of the fourth connector are configured to prevent a mating engagement from being formed therebetween. The female connection portion of the second connector and the male connection portion of the third connector are configured to prevent a mating engagement from being formed therebetween.

Each of the first connector, the second connector, the third connector, and the fourth connector can have a flattened profile.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings.

DESCRIPTION OF THE INVENTION

Figure 1:
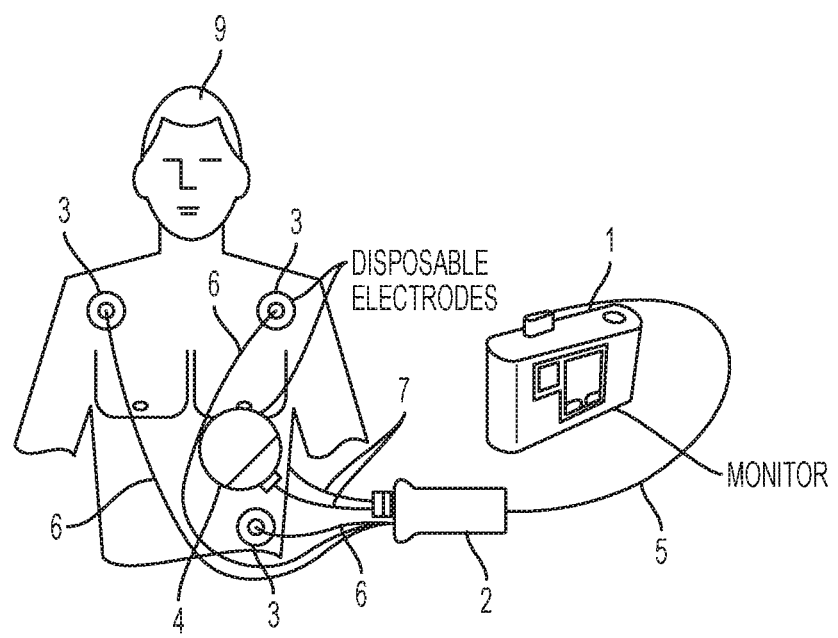
FIG. 1 is a schematic of an exemplary embodiment of a patient monitoring and treatment system that includes components that may be used in connection with the present disclosure.

As used herein, the singular form of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Also, it should be understood that any numerical range recited herein is intended to include all subranges subsumed therein. For example, a range of "1 to 10" is intended to include any and all subranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

This disclosure relates to systems and techniques for interfacing cardiac monitoring and therapeutic devices with one or more cardiac monitoring and/or therapeutic electrodes attached to a patient. A cardiac monitoring and therapeutic device is configured to monitor a patient for a predetermined cardiac related physiologic condition, e.g., a cardiac arrhythmia, and provide a treatment on detecting the condition. Such a device can include an automated external defibrillator (AED), a wearable cardioverter defibrillator (WCD), or an external cardiac pacing device. The cardiac monitoring and/or therapeutic device as described herein can be ambulatory, e.g., the device is capable of and designed for moving with the patient.

The cardiac device is capable of extended and continuous (e.g., substantially continuous) use by the patient. In some implementations, the continuous use may be substantially continuous in nature. That is, the cardiac device may be continuously used, except for sporadic periods during which the use temporarily ceases (e.g., while the patient bathes, while the patient is refit with a new and/or a different garment, while the battery is charged/changed, while the garment is laundered, etc.). For example, such substantially continuous use as described herein may nonetheless qualify as continuous use.

The cardiac device is also capable of extended and/or long-term use. For example, the cardiac device can be configured to be used by the patient for hours, days, weeks, months, or even years. In some examples, the cardiac device may be continuously used by a patient for a period of at least one week. In some examples, the cardiac device may be continuously used by a patient for a period of at least 30 days. In some examples, the cardiac device may be continuously used by a patient for a period longer at least one month. In some examples, the cardiac device may be continuously used by a patient for a period of at least two months. In some examples, the cardiac device may be continuously used by a patient for a period of at least three months. In some examples, the cardiac device may be continuously used by a patient for a period of at least six months. In some examples, the cardiac device may be continuously used by a patient for a period of at least one year. In some implementations, the extended use may be continuous in nature. The use (e.g., the continuous and/or extended use) of the wearable medical device can include continuous wear by the patient, continuous attachment to the patient, and/or continuous monitoring of the patient. For example, the continuous use can include continuous wear or attachment of the device to the patient, e.g., through one or more of the electrodes as described herein, during both periods of monitoring and periods when the device may not be monitoring the patient but is otherwise still worn by or otherwise attached to the patient. The cardiac device is configured to continuously monitor the patient for cardiac-related information (e.g., ECG information, including arrhythmia information, heart sounds, etc.) and/or non-cardiac information (e.g., blood oxygen, the patient's temperature, glucose levels, tissue fluid levels, and/or lung sounds). The cardiac device may carry out its monitoring in periodic or aperiodic time intervals or times. For example, the monitoring during intervals or times can be triggered by a user action or another event.

As noted above, the cardiac device can be configured to monitor other physiologic parameters of the patient in addition to cardiac related parameters. For example, the device can be configured to monitor, for example, lung sounds (e.g., using microphones and/or accelerometers), breath sounds, sleep related parameters (e.g., snoring, sleep apnea), tissue fluids (e.g., using radio-frequency transmitters and sensors), among others.

Other example external cardiac monitoring and therapeutic devices capable of interfacing with the electrode connectors disclosed herein include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the defibrillators described herein can be pacing-enabled, e.g., capable of providing therapeutic pacing pulses to the patient.

Exemplary Monitoring and Treatment Device and System:

FIG. 1 illustrates an exemplary therapeutic medical device 1 that is external, ambulatory, and wearable by a patient 9, and configured to implement one or more configurations described herein. For example, the medical device 1 can be an external or non-invasive medical device, e.g., the device 1 configured to be located substantially external to the patient. For example, the therapeutic medical device 1, shown in FIG. 1 as a wearable defibrillator 1, as described herein can be bodily-attached to the patient such as the LifeVest® wearable cardioverter defibrillator available from ZOLL® Medical Corporation of Pittsburgh, Pa. and Chelmsford, Mass. The wearable defibrillator 1 can be worn or carried by an ambulatory patient 9. According to one example of the present disclosure, the wearable defibrillator 1 is used as an ambulatory cardiac monitoring and treatment device within a monitoring and treatment system according to the present disclosure.

Such wearable defibrillators can be typically worn nearly continuously for two to three months at a time. During the period of time in which they are worn by the patient, the wearable defibrillator 1 can be configured to continuously monitor the vital signs of the patient, to be user-friendly and accessible, to be as light-weight, comfortable, and portable as possible, and to be capable of delivering one or more life-saving therapeutic shocks when needed. Non-limiting examples of suitable ambulatory, wearable defibrillators are disclosed in U.S. Pat. Nos. 4,928,690; 5,078,134; 5,741,306; 5,944,669; 6,065,154; 6,280,461; and 8,369,944, the content of each of which is incorporated by reference in its entirety.

The monitoring and treatment system illustrated in FIG. 1 includes the ambulatory, wearable defibrillator 1 connected to a number of monitoring/sensing electrodes 3 worn by the patient 9 so as to be in contact with the patient's skin. According to one example, the monitoring/sensing electrodes 3 can be configured to receive ECG signals from the patient 9. The sensing electrodes 3 are connected to the wearable defibrillator 1 via wires 6 that connect the sensing electrodes 3 to a distribution node 2, which is also carried by the patient 9. The node 2 is, in turn, connected to the wearable defibrillator 1 by a separate wire or cable 5 that plugs into the wearable defibrillator 1.

The monitoring and treatment system illustrated in FIG. 1 also includes two treatment electrodes 4 worn by the patient 9 on his/her front and back (not shown) so as to be in contact with the patient's skin. The treatment electrodes 4 can be configured to deliver one or more life-saving therapeutic shocks when needed. The treatment electrodes 4 are connected to the wearable defibrillator 1 via wires 7 that connect the treatment electrodes 4 to the node 2, which is connected to the wearable defibrillator 1 by the separate wire or cable 5, as discussed above. Described herein are example connector configurations that can beneficially take the place of node 2, as discussed in further detail below with reference to FIGS. 12-14.

In implementations, an example therapeutic medical device can include an in-hospital continuous monitoring defibrillator and/or pacing device, for example, an in-hospital ambulatory, wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. The electrodes can be positioned on the patient in a similar manner as described above. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient ambulatory, wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

For example, the therapeutic medical devices described above (e.g., the wearable defibrillator, the in-hospital defibrillator, and the short-term defibrillator) can protect patients at risk for sudden cardiac death. It can be used for a wide range of patient conditions or situations, including following a recent myocardial infarction or coronary revascularization. In one scenario, the ambulatory, wearable defibrillator can give caregivers time to optimize medical therapy and assess a patient's long-term risk for sudden death. The wearable defibrillator is configured to continuously monitor the patient's heart and, if a life-threatening heart rhythm is detected, the device can issue an alert to the patient. For example, a monitor can include a touchscreen for programming as well as patient interaction, and response buttons for the patient to use when responding to treatment alerts. If the patient does not respond (e.g., by holding down the response buttons) the wearable defibrillator can deliver a treatment shock to restore normal heart rhythm.

Figure 2:
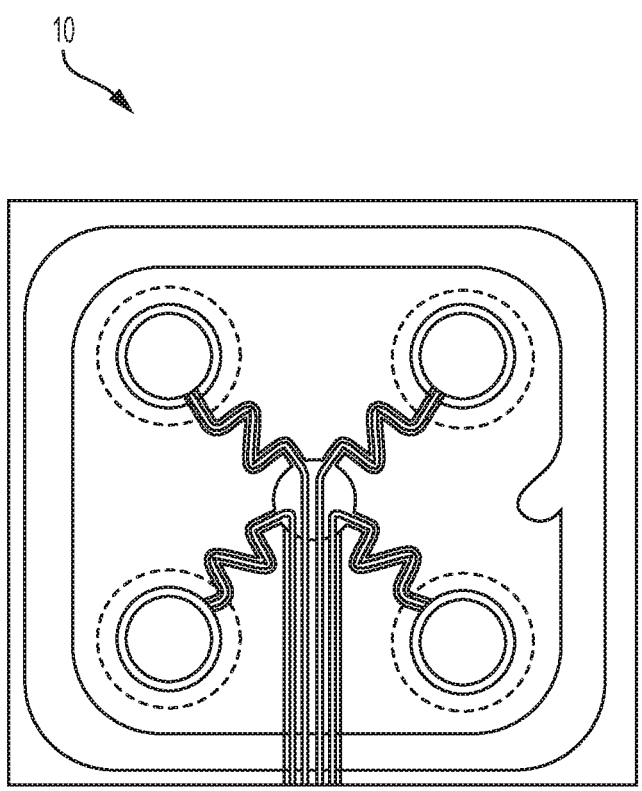
FIG. 2 is a front view of an exemplary embodiment of an electrode for a patient monitoring and treatment system to be worn by a patient that may be used in connection with the present disclosure.

Exemplary Electrode:

With reference to FIG. 2, an electrode 10 is shown that may be used in connection with the monitoring and treatment system according to the present disclosure. The electrode 10 incorporates both sensing and therapy components that are integrated on the same electrode adhesive patch that is attached to the patient's skin. Such an electrode 10 is disclosed in United States Patent Application Publication No. 2013/0325096, entitled "Long term wear multifunction biomedical electrode," the contents of which is incorporated by reference in its entirety.

Figure 3:
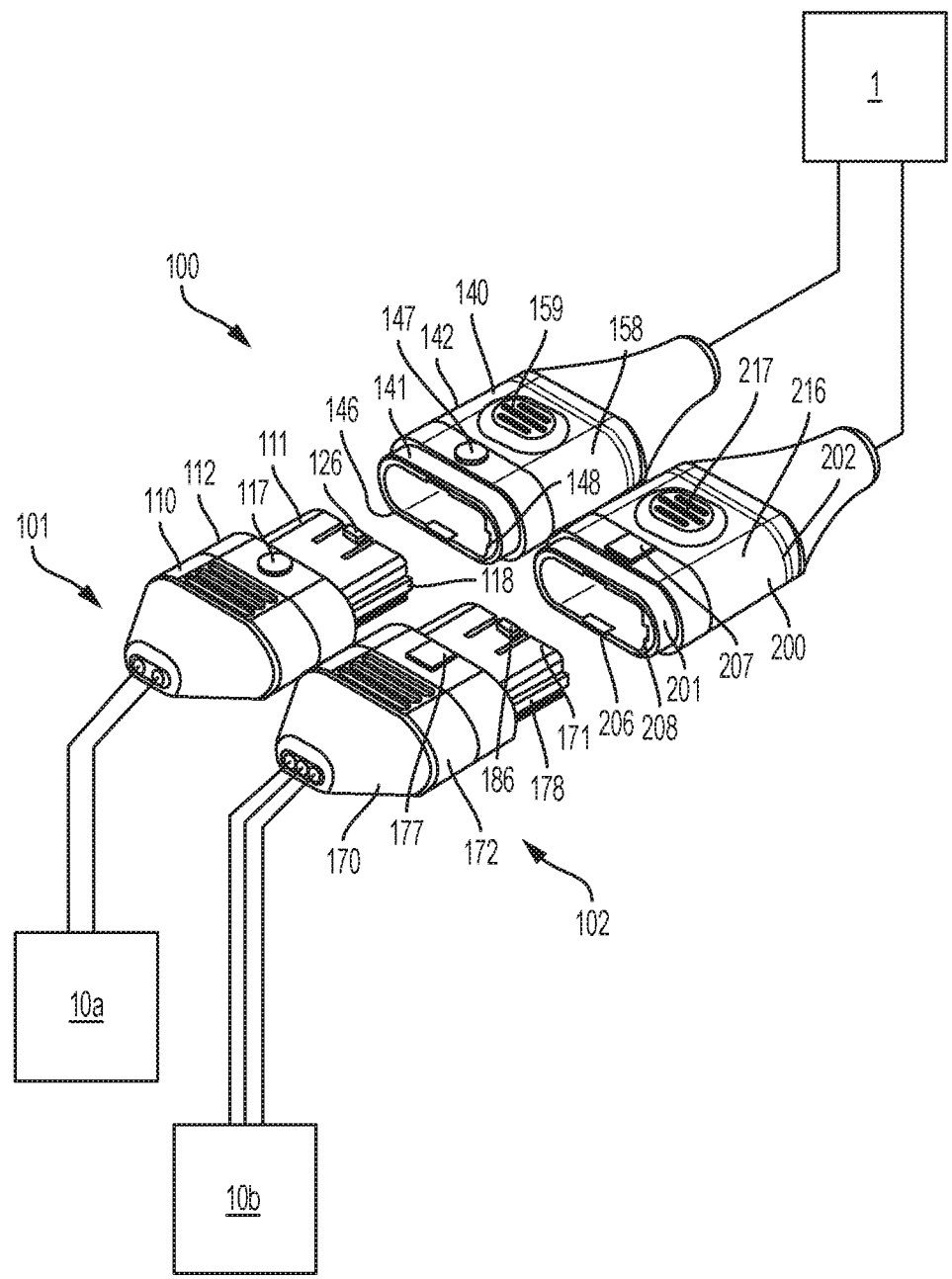
FIG. 3 is a perspective view of a connector assembly for a patient monitoring and treatment system in accordance with an example of the present disclosure.
Figure 4:
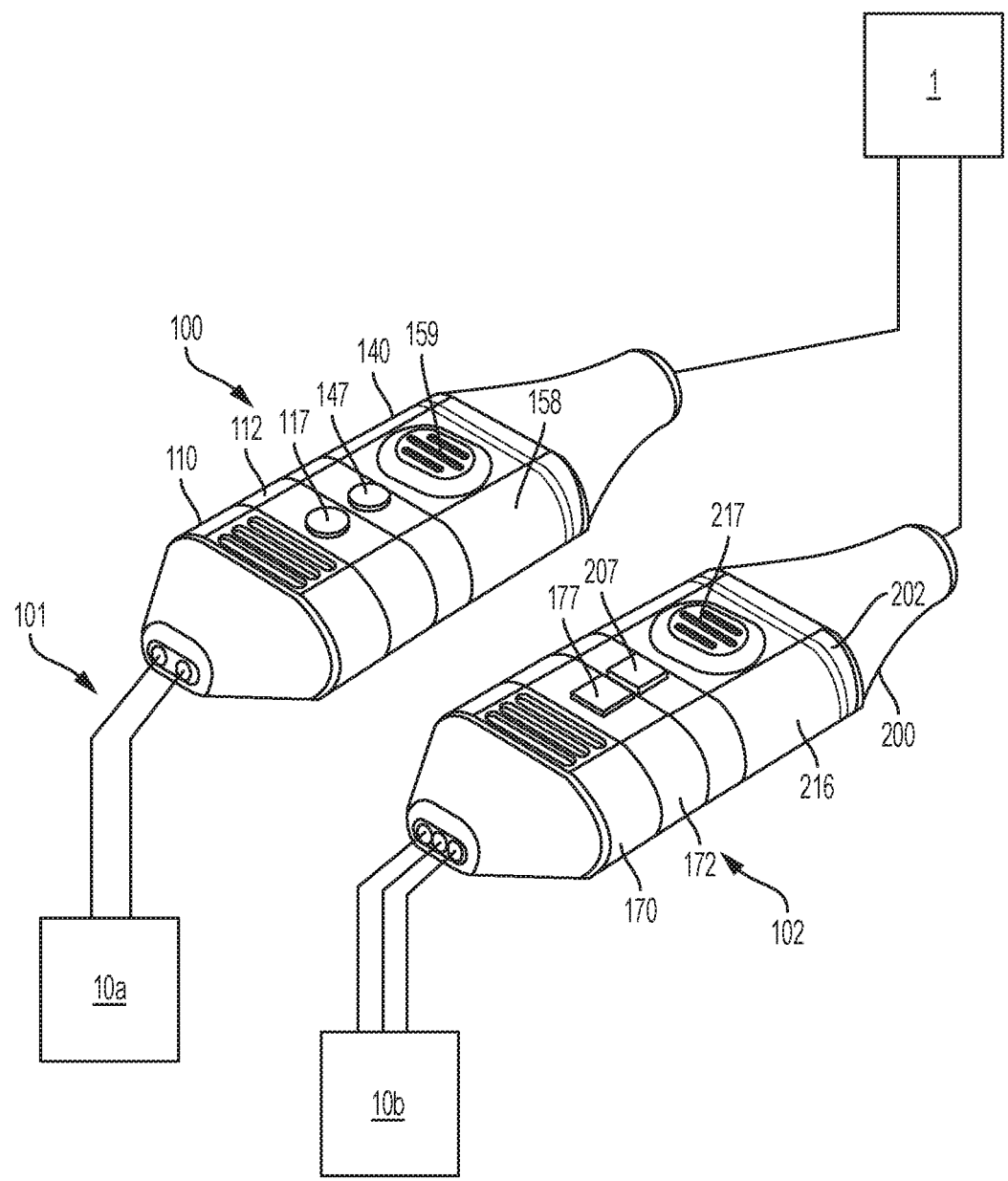
FIG. 4 is a perspective view of the connector assembly of FIG. 3 with pairs of the connectors forming respective mating engagements.

Overview of Patient Monitoring and Treatment System:

With reference to FIGS. 3 and 4, a patient monitoring and treatment system 100 is shown in accordance with an example of the present disclosure. The patient monitoring and treatment system 100 includes an ambulatory cardiac monitoring and treatment device 1, which may be of the type discussed above with reference to FIG. 1. According to one example, the ambulatory cardiac monitoring and treatment device 1 is a wearable defibrillator. The system 100 also includes a first electrode 10a and a second electrode 10b. The electrodes 10a, 10b are configured to be worn by a patient to provide at least one of monitoring a cardiac function of the patient and delivering a treatment for cardiac arrhythmia. The electrodes 10a, 10b are of the type discussed above with reference to FIG. 2 and disclosed in detail in United States Patent Application Publication No. 2013/0325096. According to one example of the present disclosure, the first electrode 10a is configured to be worn by the patient on the right side of the patient's sternum. According to another example of the present disclosure, the second electrode 10b is configured to be worn by the patient at the patient's apex, which is on the patient's left side near chest level.

In some examples, the first electrode 10a can be worn by the patient on a posterior portion of the patient's body and the second electrode 10b can be worn on an anterior portion of the patient's body. For example, the first electrode 10a (the posterior worn electrode) can be positioned just behind the patient's heart, and the second electrode 10b (the anterior worn electrode) can be positioned over front of the patient's heart.

As shown in FIGS. 3 and 4, the system 100 includes a first connector 110 connected to and in communication with the first electrode 10a, a second connector 140 connected to and in communication with the monitoring and treatment device 1, a third connector 170 connected to and in communication with the second electrode 10b, and a fourth connector connected to and in communication with the monitoring and treatment device.

The first connector 110 includes a male connection portion 111 and the second connector 140 includes a female connection portion 141. The male connection portion 111 of the first connector 110 is configured to engage the female connection portion 141 of the second connector 140 to form a mating engagement between the first and second connectors 110, 140. When the mating engagement is formed, the first connector 110 and the second connector 140 place the first electrode 10a in communication with the monitoring and treatment device 1 so as to transmit at least one of a patient monitoring signal and a patient treatment signal between the first electrode 10a and the monitoring and treatment device 1.

The third connector 170 includes a male connection portion 171 and the fourth connector 200 includes a female connection portion 201. The male connection portion 171 of the third connector 170 is configured to engage the female connection portion 201 of the fourth connector 200 to form a mating engagement between the third and fourth connectors 170, 200. When the mating engagement is formed, the third connector 170 and the fourth connector 200 place the second electrode 10b in communication with the monitoring and treatment device 1 so as to transmit at least one of a patient monitoring signal and a patient treatment signal between the second electrode 10b and the monitoring and treatment device 1.

According to an example of the present disclosure, the male connection portion 111 of the first connector 110 and the female connection portion 201 of the fourth connector 200 are configured to prevent a mating engagement from being formed therebetween. Likewise, the female connection portion 141 of the second connector 140 and the male connection portion 171 of the third connector 170 are configured to prevent a mating engagement from being formed therebetween. This feature prevents improper connection and communication of the electrodes 10a, 10b to the ambulatory cardiac monitoring and treatment device 1, which could result in the patient monitoring signals not being received or being misinterpreted by the ambulatory cardiac monitoring and treatment device 1 and/or the patient treatment signals not being properly transmitted to the electrodes 10a, 10b.

With reference to FIGS. 10A-11B, according to one particular example of the present disclosure, the male connection portion 111 of the first connector 110 has a thickness $t_1$ and a width $w_1$ that corresponds to the thickness $t_2$ and the width $w_2$ of the female connection portion 141 of the second connector 140, but does not correspond to the thickness $t_4$ and width $w_4$ of the female connection portion 201 of the fourth connector 200. Accordingly, the male connection portion 111 of the first connector 110 can be fit into the female connection portion 141 of the second connector 140 but not into the female connection portion 201 of the fourth connector 200. Similarly, the male connection portion 171 of the third connector 170 has a thickness $t_3$ and a width $w_3$ that corresponds to the thickness $t_4$ and the width $w_4$ of the female connection portion 201 of the fourth connector 200, but does not correspond to the thickness $t_2$ and width $w_2$ of the female connection portion 141 of the second connector 140. Accordingly, the male connection portion 171 of the third connector 170 can be fit into the female connection portion 201 of the fourth connector 200 but not into the female connection portion 141 of the second connector 140.

According to another particular example of the present disclosure, the first and second connectors 110, 140 and the third and fourth connectors 170, 200 may incorporate other visual and/or tactile indicators that provide the feedback regarding the proper mating relationships between the first and second connectors 110, 140 and the third and fourth connectors 170, 200, respectively. For instance, the male connection portion 111 of the first connector 110 and the female connection portion 141 of the second connector 140 may have a common color, such as blue, and the male connection portion 171 of the third connector 170 and the female connection portion 201 of the fourth connector 200 may have a different common color, such as grey. Additionally, the first connector 110 and the second connector 140 may each include alignment indicators 117, 147 having a common shape, such as a circle, and the third connector 170 and the fourth connector 200 may each include alignment indicators 177, 207 having a different common shape, such as a square, as is shown in FIGS. 3-6B.

According to another example of the present disclosure, each of the first connector 110, the second connector 140, the third connector 170, and the fourth connector 200 has a flattened profile so that the connectors 110, 140, 170, 200 can be positioned relatively flat against the patient's body and provide minimal interference with the patient's movement and limit the likelihood of the connectors 110, 140, 170, 200 being caught in the patient's clothing or on external structures or surfaces, such as bed rails, door frames, etc.

Figure 10A:
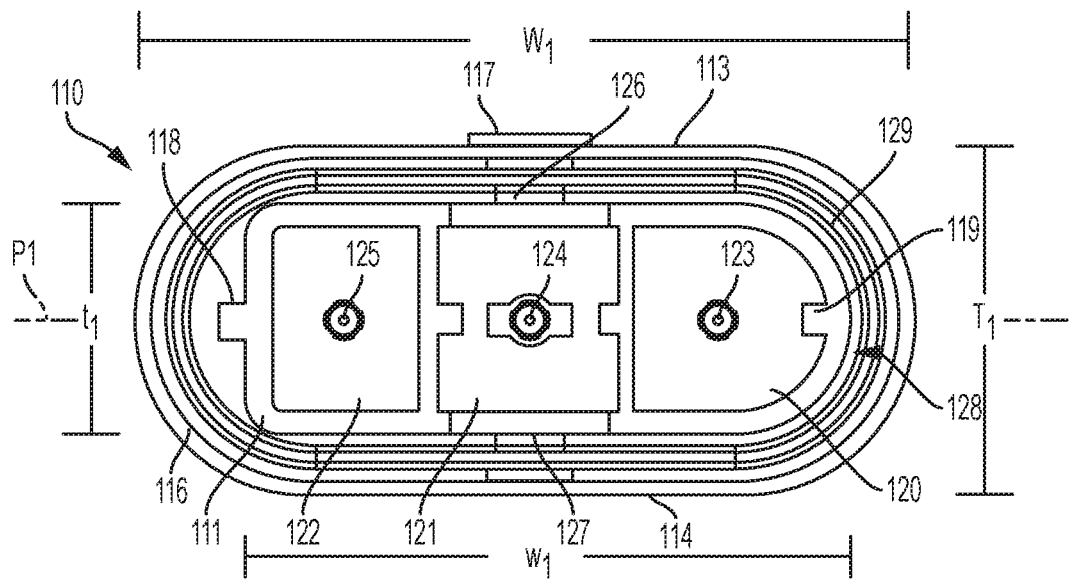
FIG. 10A is a front view of the first connector of the connector assembly of FIG. 3.
Figure 10B:
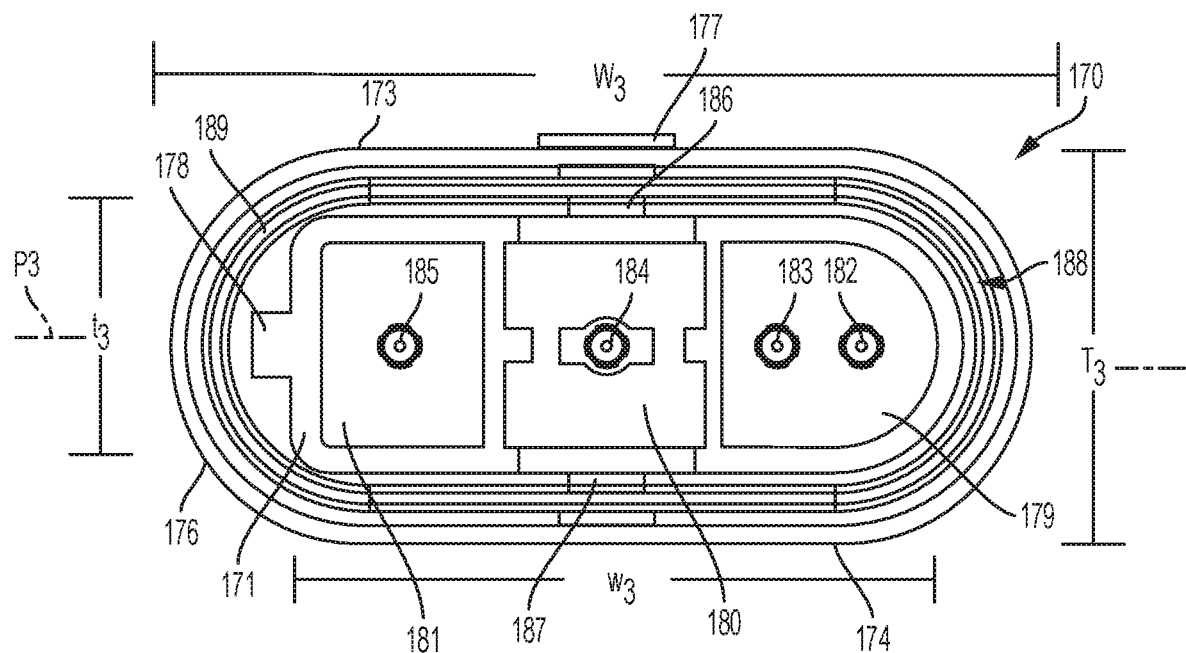
FIG. 10B is a front view of the third connector of the connector assembly of FIG. 3.
Figure 11B:
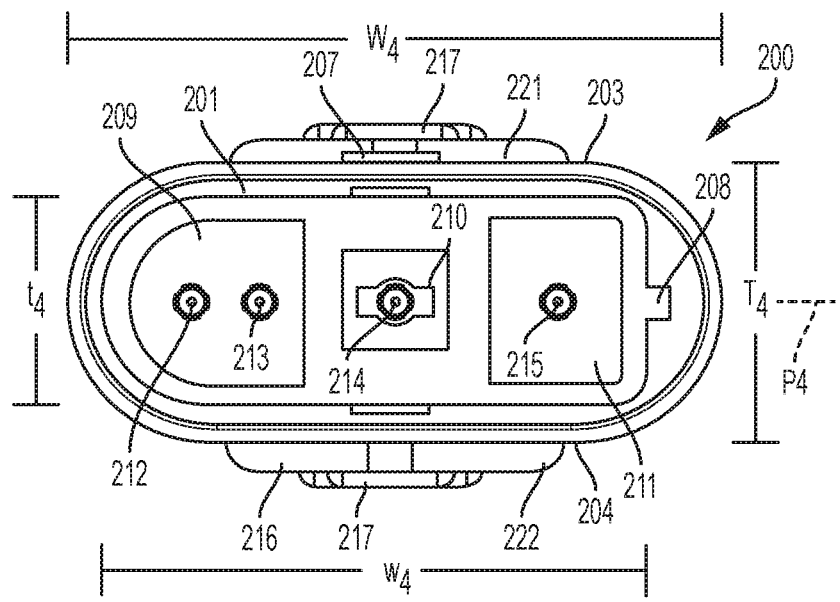
FIG. 11B is a front view of the fourth connector of the connector assembly of FIG. 3.
Figure 11A:
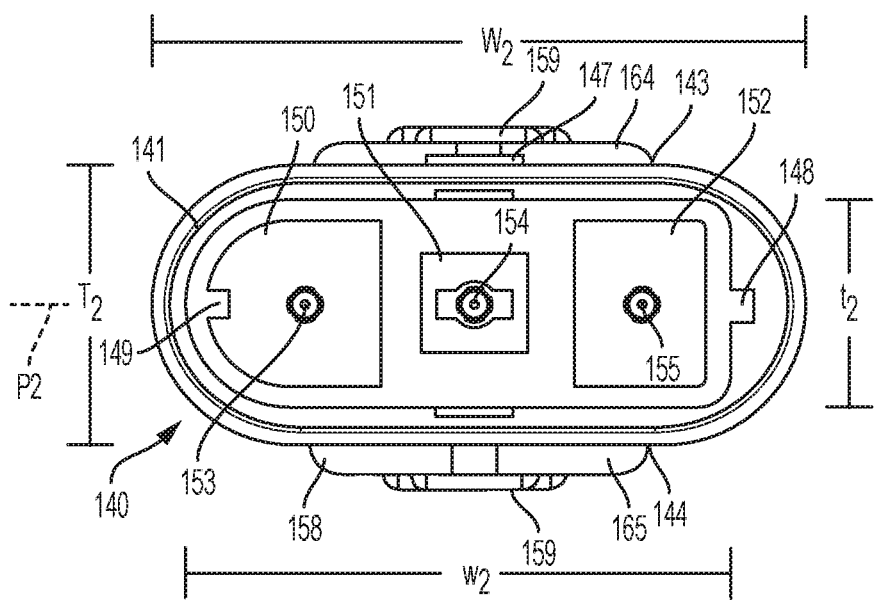
FIG. 11A is a front view of the second connector of the connector assembly of FIG. 3.

For instance, as shown in FIG. 10A, the overall width $W_1$ of the first connector 110 is relatively greater than its overall thickness $T_1$ and the body 112 of the first connector 110 has a substantially oval or oblong circular shape so as to provide the flattened profile without any sharp edges or corners. As shown in FIG. 10B, the overall width $W_3$ of the third connector 170 is also relatively greater than its overall thickness $T_3$ and the body 172 of the third connector 170 has a substantially oval or oblong circular shape so as to provide the flattened profile without any sharp edges or corners. As shown in FIG. 11A, the overall width $W_2$ of the second connector 140 is relatively greater than its overall thickness $T_2$ and the body 142 of the second connector 140 has a substantially oval or oblong circular shape so as to provide the flattened profile without any sharp edges or corners. As shown in FIG. 11B, the overall width $W_4$ of the fourth connector 200 is also relatively greater than its overall thickness $T_4$ and the body 202 of the fourth connector 200 has a substantially oval or oblong circular shape so as to provide the flattened profile without any sharp edges or corners. As shown in FIG. 4, the overall width $W_1$ and thickness $T_1$ of the first connector 110 is the same as the overall width $W_2$ and thickness $T_2$ of the second connector 140 and the overall width $W_3$ and thickness $T_3$ of the third connector 170 is the same as the overall width $W_4$ and thickness $T_4$ of the fourth connector 200. Additionally, it is to be appreciated that the connectors 110, 140, 170, 200 may have any shape or configuration known to be suitable to those having ordinary skill in the art.

According to one particular example of the present disclosure, first connector 110 has an overall width $W_1$ between 25-30 millimeters (mm), specifically 27.7 mm, and an overall thickness $T_1$ between 11-16 mm, specifically 13.2 mm. The male connection portion 111 of the first connector 110 has a width $w_1$ between 18-23 mm, specifically 21.0 mm and a thickness $t_1$ between 6-11 mm, specifically 8.0 mm. The second connector 140 has an overall width $W_2$ between 25-30 mm, specifically 27.7 mm, and overall thickness $T_2$ between 11-16 mm, specifically 13.2 mm. The female connection portion 141 of the second connector 140 has a width $w_2$ between 18-23 mm, specifically 21.1 mm, and a thickness $t_2$ between 6-11 mm, specifically 8.1 mm. The third connector 170 has an overall width $W_3$ between 27-32 mm, specifically 29.7 mm, and an overall thickness $T_3$ between 10-15 mm, specifically 12.2 mm. The male connection portion 171 of the third connector 170 has a width $w_3$ between 21-26 mm, specifically 23.0 mm, and a thickness $t_3$ between 5-10 mm, specifically 7.0 mm. The fourth connector 200 has an overall width $W_4$ between 27-32 mm, specifically 29.7 mm, and an overall thickness $T_4$ between 10-15 mm, specifically 12.2 mm. The female connection portion 201 of the fourth connector 200 has a width $w_4$ between 21-26 mm, specifically 23.2 mm, and a thickness $t_4$ between 5-10 mm, specifically 7.1 mm. It is to be appreciated that the dimensions of the connectors 110, 140, 170, 200 and the ratios between the dimensions may be adjusted to any value known to be suitable to those having ordinary skill in the art. The values provided above are merely exemplary and are provided to demonstrate the possible relationships between the relative sizes of the connectors 110, 140, 170, 200 and the connection portions 111, 141, 171, 201 and to provide context to the flattened profiles of the connectors 110, 140, 170, 200.

According to another particular embodiment of the present disclosure, the bodies 112, 142, 172, 202 and the connection portions 111, 141, 171, 201 of the connectors 110, 140, 170, 200 are made from a rigid thermoplastic polymer material, such as a polycarbonate material. It is to be appreciated that the connectors 110, 140, 170, 200 may be made from any material found to be suitable to those having ordinary skill in the art.

With reference to FIGS. 3 and 4, according to one example of the present disclosure, the first electrode 10a and the first connector 110 form a first electrode assembly 101 and the second electrode 10b and the third connector 170 form a second electrode assembly 102. The electrode assemblies 101, 102 may be provided as individual replaceable units separate from the patient monitoring and treatment system 100, thus allowing for the electrodes 10a, 10b and first and third connectors 110, 170 to be manufactured so as to be disposable. According to another example of the present disclosure, the first electrode assembly 101 also includes the second connector 140 and the second electrode assembly 102 also includes the fourth connector 200.

Orientation and Alignment Features:

With reference to FIGS. 3, 5A-6B, and 10A-11B, according to an example of the present disclosure each of the connectors 110, 140, 170, 200 includes at least one orientation aligning feature. The orientation aligning features 118, 119, 148, 149 on the first connector 110 and the second connector 140 correspond to one another and are configured to engage the first connector 110 with the second connector 140 in a fixed orientation with respect to each other to form the mating engagement. Similarly, the orientation aligning features 178, 208 on the third connector 170 and the fourth connector 200 correspond to one another and are configured to engage the third connector 170 with the fourth connector 200 in a fixed orientation with respect to each other to form the mating engagement. Thus, the first connector 110 is required to be in a certain fixed orientation with respect to the second connector 140 to form the mating engagement. The third connector 170 is also required to be in a certain fixed orientation with respect to the fourth connector 200 to form the mating engagement. This feature of the present disclosure ensures that the corresponding electrical contacts within the connectors 110, 140, 170, 200, which will be discussed in detail below, are properly engaged with each other so that patient monitoring signals and patient treatment signals are properly transmitted between the ambulatory cardiac monitoring and treatment device 1 and the first and second electrodes 10a, 10b.

As shown in FIGS. 3, 5A, 6A, 10A, and 11A, the at least one orientation aligning feature on the first connector 110 includes an orientation protrusion 118 disposed on an external side of the male connection portion 111 and extending along the length of the male connection portion 111. The at least one orientation aligning feature on the first connector 110 may additionally include a smaller orientation protrusion 119 disposed on a side of the interior surface of the male connection portion 111 and extending along the length of the interior of the male connection portion 111. As shown, the orientation protrusions 118, 119 are disposed on opposite lateral sides of the male connection portion 111. The at least one orientation aligning feature on the second connector 140 includes an orientation slot 148 defined in an interior surface of the female connection portion 141 along a side of the female connection portion 141. The at least one orientation feature of the second connector 140 may additionally include a smaller orientation slot 149 defined in a surface of a socket housing 150 disposed within the female connection portion 141 of the second connector 140. When the male connection portion 111 of the first connector 110 is slid into the female connection portion 141 of the second connector 140 to form the mating engagement, the orientation protrusion 118 on the male connection portion 111 becomes disposed in and slidably engages with the corresponding orientation slot 148 in the female connection portion 141 to allow the connectors 110, 140 to be pushed together. Also, the orientation protrusion 119 on the interior of the male connection portion 111 becomes disposed in and slidably engages with the corresponding orientation slot 149 in the socket housing 150 in the female connection portion 141 to allow the connectors 110, 140 to be pushed together. The male connection portion 111 of the first connector 110 may also have a rounded shape on the side opposite to the orientation protrusion 118. The interior surface of the female connection portion 141 of the second connector 140 may be correspondingly rounded on a side opposite to the orientation slot 148. Because the corresponding orientation alignment features 118, 119, 148, 149 are disposed asymmetrically on the male and female connection portions 111, 141, the first and second connectors 110, 140 must be in a fixed orientation with respect to each other in order for the mating engagement to be formed.

In order to assist the user in determining the proper orientation for connecting the first and second connectors 110, 140, the first connector 110 may include an alignment indicator 117 on a first or top side 113 of the body 112. The second connector 140 may include a corresponding alignment indicator 147 on a first or top side 143 of the body 142. The alignment indicators 117, 147 may be raised shaped protrusions. In use, the alignment indicators 117, 147 provide a user with visual or tactile feedback that the first or top sides 113, 143 of the first and second connectors 110, 140 are oriented in the same direction such that the corresponding alignment features 118, 119, 148, 149 are properly positioned with respect to each other and the first and second connectors 110, 140 can be pushed together to form the mating engagement.

As shown in FIGS. 3, 5B, 6B, 10B, and 11B, the at least one orientation aligning feature on the third connector 170 includes an orientation protrusion 178 disposed on an external side of the male connection portion 171 and extending along the length of the male connection portion 171. The at least one orientation aligning feature on the fourth connector 200 includes an orientation slot 208 defined in an interior surface of the female connection portion 201 along a side of the female connection portion 201. When the male connection portion 171 of the third connector 170 is slid into the female connection portion 201 of the fourth connector 200 to form the mating engagement, the orientation protrusion 178 on the male connection portion 171 becomes disposed in and slidably engages with the corresponding orientation slot 208 in the female connection portion 201 to allow the connectors 170, 200 to be pushed together. The male connection portion 171 of the first connector 170 may also have a rounded shape on the side opposite to the orientation protrusion 178. The interior surface of the female connection portion 201 of the fourth connector 200 may be correspondingly rounded on a side opposite to the orientation slot 208. Because the corresponding orientation alignment features 178, 208 are disposed asymmetrically on the male and female connection portions 171, 201, the third and fourth connectors 170, 200 must be in a fixed orientation with respect to each other in order for the mating engagement to be formed.

In order to assist the user in determining the proper orientation for connecting the third and fourth connectors 170, 200, the third connector 170 may include an alignment indicator 177 on a first or top side 173 of the body 172. The fourth connector 200 may include a corresponding alignment indicator 207 on a first or top side 203 of the body 202. The alignment indicators 177, 207 may be raised shaped protrusions. In use, the alignment indicators 177, 207 provide a user with visual or tactile feedback that the first or top sides 173, 203 of the third and fourth connectors 170, 200 are oriented in the same direction such that the corresponding alignment features 178, 208 are properly positioned with respect to each other and the third and fourth connectors 170, 200 can be pushed together to form the mating engagement.

It is to be appreciated that the orientation alignment features discussed above may be of any shape or configuration known to those having ordinary skill in the art to be suitable for the purpose of preventing the mating engagement of the connectors 110, 140, 170, 200 in the improper orientation. It is also to be appreciated that the orientation alignment features may further be arranged to prevent a mating engagement from being formed between the first connector 110 and the fourth connector 200 and between the second connector 140 and the third connector 170, as discussed above.

Locking, Retaining, and Release Features:

With reference to FIGS. 3-5A, 6A, 7, 10A, and 11A, according to an example of the present disclosure the male connection portion 111 of the first connector 110 includes at least two locking features 126, 127 that are configured to engage corresponding retaining features 156, 157 on the second connector 140 to retain the first connector 110 in the mating engagement. The at least two locking features 126, 127 are also configured to be engaged simultaneously by a release mechanism 158 on the second connector 140 to release the first connector 110 from the mating engagement.

The female connection portion 141 of the second connector 140 includes at least two retaining features 156, 157 configured to be engaged by the locking features 126, 127 on the male connection portion 111 of the first connector 110 to retain the first connector 110 and the second connector 140 in the mating engagement. The female connection portion 141 also includes the release mechanism 158, which is configured to be actuated to simultaneously engage the at least two locking features 126, 127 to release the first connector 110 and the second connector 140 from the mating engagement.

Figure 5A:
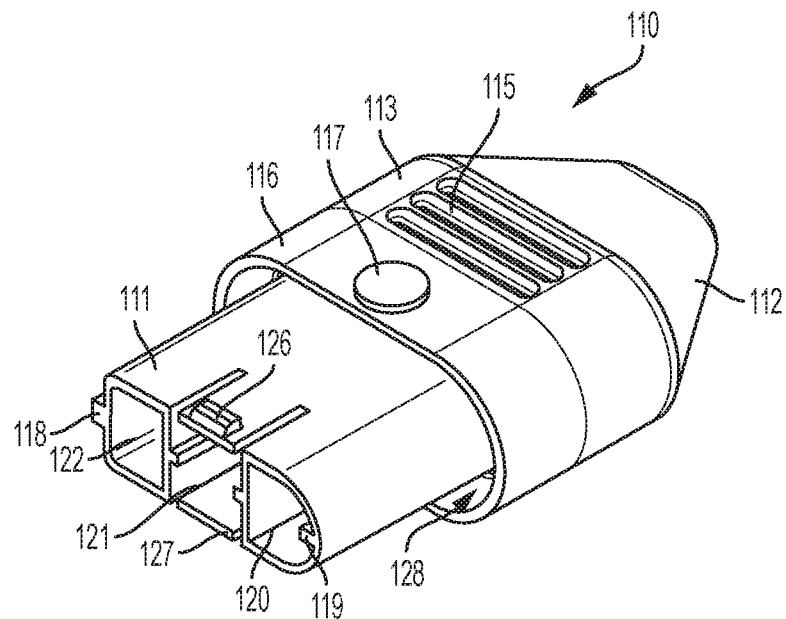
FIG. 5A is a perspective view of a first connector of the connector assembly of FIG. 3.
Figure 6A:
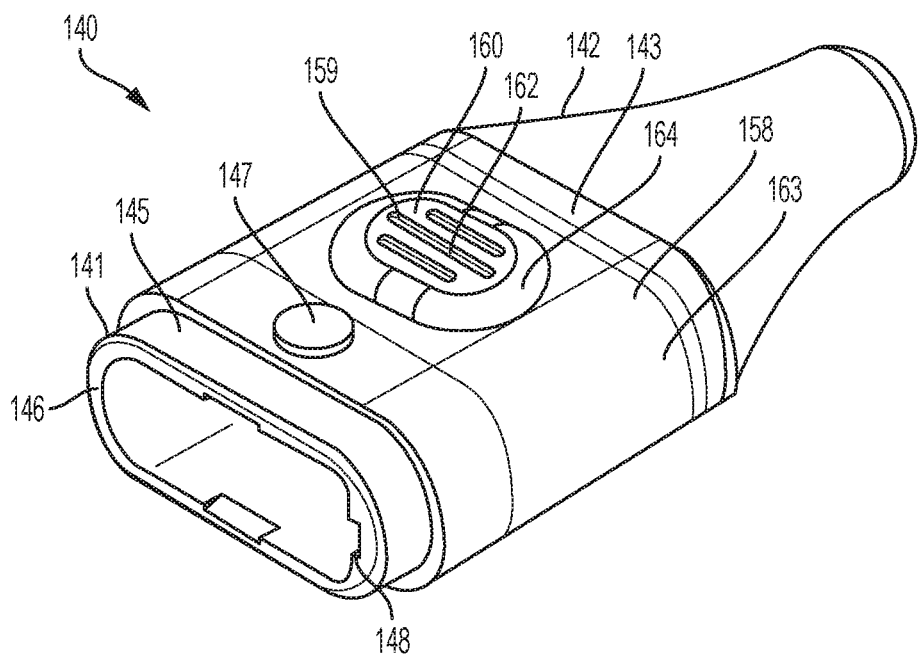
FIG. 6A is a perspective view of a second connector of the connector assembly of FIG. 3.
Figure 7:
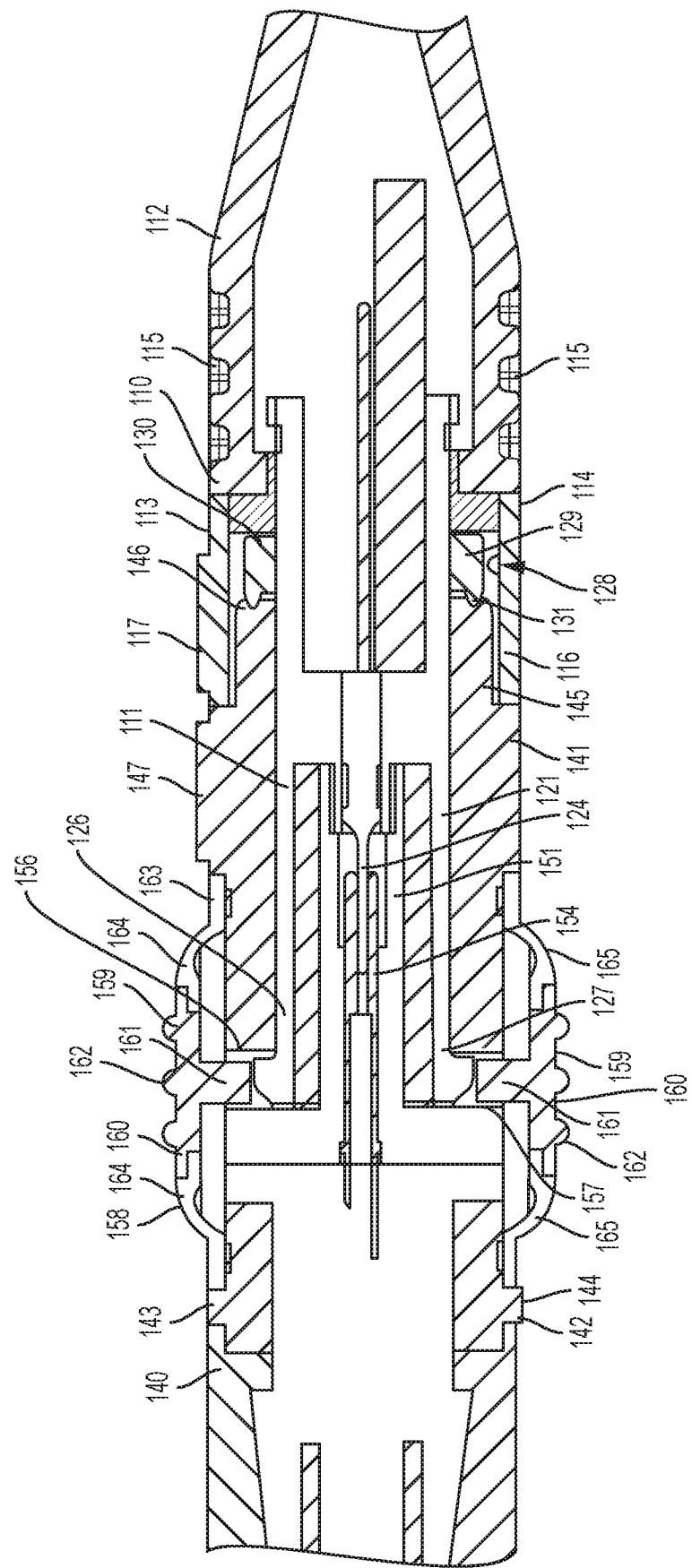
FIG. 7 is a cross-sectional view of a pair of the connectors of the connector assembly of FIG. 3 forming a mating engagement.

As shown in FIGS. 5A, 6A, and 7, according to a particular example of the present disclosure, the at least two locking features on the male connection portion 111 of the first connector 110 include flexible locking tabs 126, 127 disposed on the male connection portion 111 along the lateral center of the male connection portion 111. Each of the flexible locking tabs 126, 127 is resiliently and flexibly connected to the male connection portion 111 so as to be able to deflect slightly. Each flexible locking tab 126, 127 also includes a protrusion disposed at an end thereof, which is substantially flush with the leading end of the male connection portion 111. The first flexible locking tab 126 is disposed at the top of the male connection portion 111 and is oriented toward the top or first side 113 of the body 112 of the first connector 110. The second flexible locking tab 127 is disposed opposite to the first flexible locking tab 126 on the bottom of the male connection portion 111 and is oriented toward the bottom or second side 114 of the body 112 of the first connector 110.

As shown in FIG. 7, the at least two retaining features 156, 157 on the female connection portion 141 of the second connector 140 include apertures 156, 157 extending at least partially through the female connection portion 141 from an the interior of the female connection portion 141 toward a respective one of the top (first) and second (bottom) sides 143, 144 of the body 142 of the second connector 140.

When the male connection portion 111 of the first connector 110 is slid into the female connection portion 141 of the second connector 140, the flexible locking tabs 126, 127 on the male connection portion 111 are caused to flex inwardly as the protrusions on the flexible locking tabs 126, 127 engage the interior surface of the female connection portion 141. Upon reaching the apertures 156, 157 in the female connection portion 141, the protrusions at the ends of the flexible locking tabs 126, 127 extend into and become engaged with the corresponding apertures 156, 157 to secure the first connector 110 and the second connector 140 in the mating engagement, as shown in FIG. 7.

As shown in FIGS. 6A, 7, and 11A, the release mechanism 158 on the second connector 140 includes at least two buttons 159 disposed in a band of resiliently flexible material 163 extending around the perimeter of circumference of the body 142 of the second connector 140. The two buttons 159 are disposed on each of the top (first) and bottom (second) sides 143, 144 of the body 142 of the second connector 140. Each button 159 includes a top 160 disposed above the resiliently flexible material 163 and a depending portion 161 that extends inwardly from the top 160 through the resiliently flexible material 163 and into a respective one of the apertures 156, 157. The depending portion 161 of each button 159 is configured to engage a respective flexible locking tab 126, 127 on the male connection portion 111 of the first connector 110 when the button 159 is depressed into the resiliently flexible material 163 in order to cause the respective locking tab 126, 127 to disengage from the respective aperture 156, 157.

The band of resiliently flexible material 163 includes raised portions 164, 165 formed on the top (first) and bottom (second) sides 143, 144 of the body 142 of the second connector 140, respectively. The two buttons 159 are disposed in the raised portions 164, 165 of the resiliently flexible material 163. The top 160 of each button 159 is partially embedded in the respective raised portion 164, 165 to retain the button 159 in position on the second connector 140. As the two buttons 159 are depressed, the raised portions 164, 165 deflect to allow the depending portion 161 to travel inwardly through the respective apertures 156, 157 to engage the respective locking tabs 126, 127. After each button 159 has been released, the raised portions 164, 165 return to their initial shape causing the two buttons 159 to move outwardly such that the depending portions 161 are no longer in a position to engage the respective locking tabs 126, 127. The top 160 of each button 159 includes a gripping feature 162, such as a series of raised protrusions, defined thereon to assist in the depression of the button 159 and handling of the second connector 140. As shown in FIGS. 3-5A, 7, and 10A, the body 112 of the first connector 110 may also include a gripping feature 115, such as a series of shaped recesses, defined in each of the top (first) and bottom (second) sides 113, 114 of the body 112 to facilitate handling of the first connector 110.

Accordingly, flexible locking tabs 126, 127 on the male connection portion 111 of the first connector 110 engage separate respective apertures/retaining features 156, 157 in the female connection portion 141 of the second connector 140. The flexible locking tabs 126, 127 must be simultaneously engaged by the depending portions 161 of the buttons 159 pressed inwardly in order to disengage both flexible locking tabs 126, 127 from the respective apertures/retaining features 156, 157. Therefore, to release the mating engagement between the first and second connectors 110, 140, both buttons 159 of the release mechanism 158 must be depressed simultaneously and the male connection portion 111 slid out from the female connection portion 141. This feature of the present disclosure is intended to prevent accidental or unintentional release of the first and second connectors 110, 140 from the mating engagement due the connectors 110, 140 being accidentally bumped or jostled, being pressed against a surface on one side, or becoming trapped between the patient's body and a chair or bed.

With reference to FIGS. 3, 4, 5B, 6B, 10B, and 11B, the third connector 170 and the fourth connector 200 incorporate similar locking features, retaining features, and release mechanism as the first connector 110 and the second connector 140 discussed above. The male connection portion 171 of the third connector 170 includes at least two locking features 186, 187 that are configured to engage corresponding retaining features on the fourth connector 200 to retain the third and fourth connectors 170, 200 in the mating engagement. The female connection portion 201 of the fourth connector 200 also includes the release mechanism 216, which is configured to be actuated to simultaneously engage the at least two locking features 186, 187 to release the third connector 170 and the fourth connector 200 from the mating engagement.

Figure 5B:
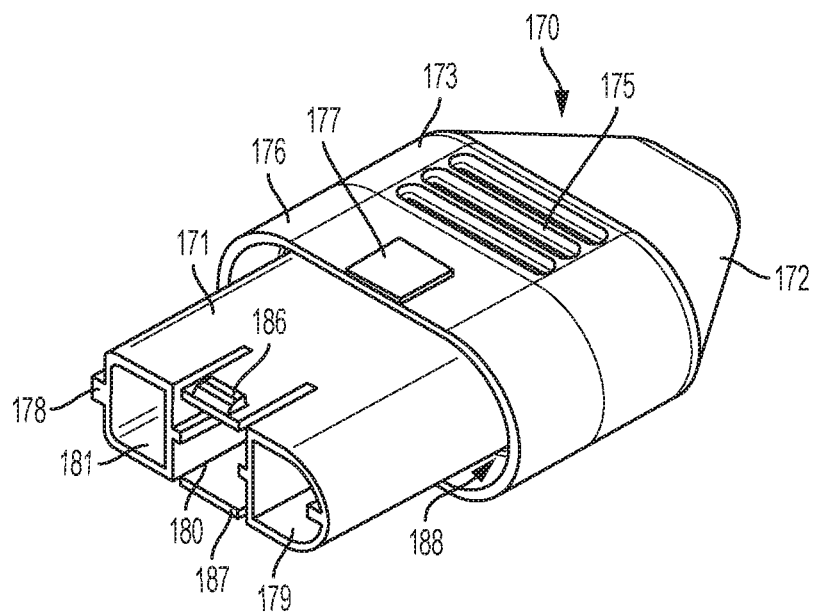
FIG. 5B is a perspective view of a third connector of the connector assembly of FIG. 3.

As shown in FIG. 5B, the at least two locking features on the male connection portion 171 of the third connector 170 include flexible locking tabs 186, 187 disposed on the male connection portion 171 along the lateral center of the male connection portion 171. Each of the flexible locking tabs 186, 187 is resiliently and flexibly connected to the male connection portion 171 so as to be able to deflect slightly. Each flexible locking tab 186, 187 also includes a protrusion disposed at an end thereof, which is substantially flush with the leading end of the male connection portion 171. The first flexible locking tab 186 is disposed at the top of the male connection portion 171 and is oriented toward the top or first side 173 of the body 172 of the third connector 170. The second flexible locking tab 187 is disposed opposite to the first flexible locking tab 186 on the bottom of the male connection portion 171 and is oriented toward the bottom or second side 174 of the body 172 of the third connector 170.

The corresponding retaining features on the female connection portion 201 of the fourth connector 200 include apertures (not shown) in the female connection portion 200, which are the same as the apertures 156, 157 discussed above with reference to the second connector 140 and the flexible locking tabs 186, 187 on the male connection portion 171 of the third connector 170 engage with the female connection portion 201 and the apertures in the same manner as discussed above with reference to the first and second connectors 110, 140, as shown in FIG. 7.

Figure 6B:
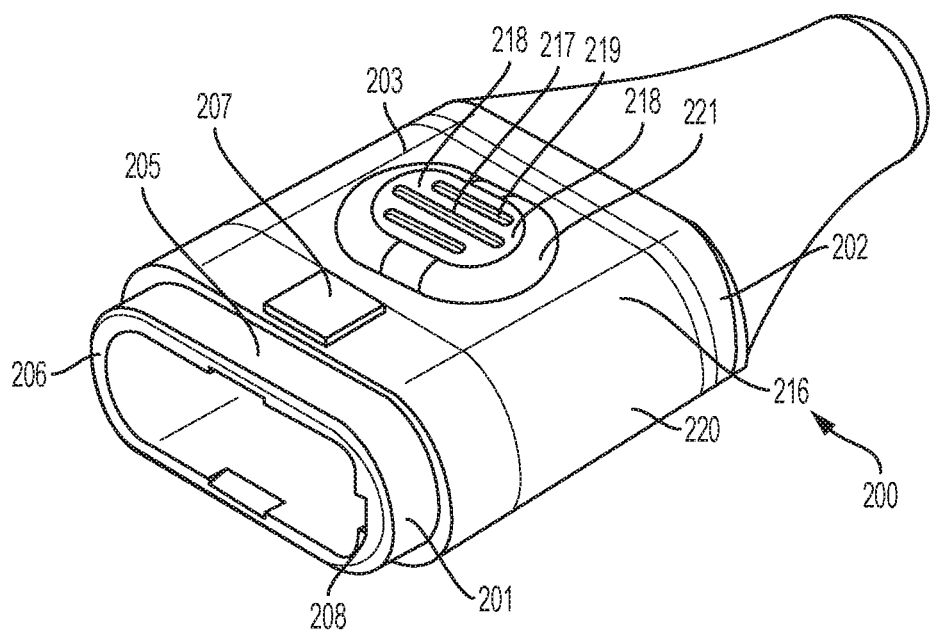
FIG. 6B is a perspective view of a fourth connector of the connector assembly of FIG.

As shown in FIGS. 6B and 11B, the release mechanism 216 on the fourth connector 200 is similar to the release mechanism 158 of the second connector 140 discussed above, and includes at least two buttons 217 disposed in a band of resiliently flexible material 220 extending around the perimeter or circumference of the body 202 of the fourth connector 200. The buttons 217 are disposed on each of the top (first) and bottom (second) sides 203, 204 of the body 202 of the fourth connector 200. The buttons 217 are similar to the buttons 159 on the second connector 140 discussed above. Each button 217 includes a top 218 disposed above the resiliently flexible material 220 and a depending portion (not shown) that extends inwardly from the top 218 through the resiliently flexible material 220 and into a respective one of the apertures. The depending portion of each button 217 is configured to engage a respective flexible locking tab 186, 187 on the male connection portion 171 of the third connector 170 when the button 217 is depressed into the resiliently flexible material 220 in order to cause the respective locking tab 186, 187 to disengage from the respective aperture.

The band of resiliently flexible material 220 includes raised portions 221, 222 formed on the top (first) and bottom (second) sides 203, 204 of the body 202 of the fourth connector 200, respectively. The buttons 217 are disposed in the raised portions 221, 222 of the resiliently flexible material 220. The top 218 of each button 217 is partially embedded in the respective raised portion 221, 222 to retain the button 217 in position on the fourth connector 200. As the buttons 217 are depressed, the raised portions 221, 222 deflect to allow the depending portions to engage the respective locking tabs 186, 187. After each button 217 has been released, the raised portions 221, 222 return to their initial shape causing the buttons 217 to move outwardly. The top 218 of each button 217 includes a gripping feature 219, such as a series of raised protrusions, defined thereon to assist in depression of the button 217 and handling of the fourth connector 200. As shown in FIGS. 3, 4, 5B, and 10B, the body 172 of the third connector 170 may also include a gripping feature 175, such as a series of shaped recesses, defined in each of the top (first) and bottom (second) sides 173, 174 of the body 172 to facilitate handling of the third connector 170.

The release mechanism 216 of the fourth connector 200 is actuated in the same manner as the release mechanism 159 discussed above with respect to the second connector 140 to simultaneously engage the flexible locking tabs 186, 187 of the male connection portion 171 of the third connector 170 to disengage the flexible locking tabs 186, 187 from the respective apertures and release the mating engagement between the third and fourth connectors 170, 200.

According to a particular example of the present disclosure, the pull apart force for the first and second connectors 110, 140 and the third and fourth connectors 170, 200 when the above-described locking features are engaged is between 3-7 pounds of force, specifically 5 pounds. The pull apart force between the connectors when the above-described locking features are not engaged is approximately 2 pounds of force. It is to be appreciated that the above-described locking features may be structured such that the pull apart force is of any value found to be suitable to those having ordinary skill in the art so long as the pull apart force of the connectors is less than the force necessary to cause damage to the wires extending between the connectors 110, 140, 170, 200 and the ambulatory cardiac monitoring and treatment device 1 and the electrodes 10a, 10b in order to avoid damage to the other components of the system 100 and possible harm to the patient.

According to another particular example of the present disclosure, the bands of resiliently flexible material 163, 220 are made from a thermoplastic elastomer, such as a material consisting of thermoplastic urethane and crosslinked silicon rubber. The buttons 159, 217 are made from a thermoplastic polymer, such as acrylonitrile butadiene styrene (ABS). The buttons 159, 217 may also be provided with a color that corresponds to the corresponding color of the female connection portions 141, 201 of the corresponding connectors 140, 200, as discussed above. It is to be appreciated that the bands 163, 220 and the buttons 159, 217 may be made from any material and in in any color found to be suitable to those having ordinary skill in the art.

Sealing and Interlocking Feature:

With reference to FIGS. 5A, 7, 8, and 10A, the body 112 of the first connector 110 includes a skirt portion 116 surrounding the male connection portion 111 to define an annular space 128 between the skirt portion 116 and the male connection portion 111. A sealing member 129 is disposed within the annular space 128 for sealing the mating engagement between the first connector 110 and the second connector 140 to prevent moisture and environmental contaminants, such as dust, from entering the interiors of the mated first and second connectors 110, 140 and interfering with the electrical connections between the first and second connectors 110, 140.

Figure 8:
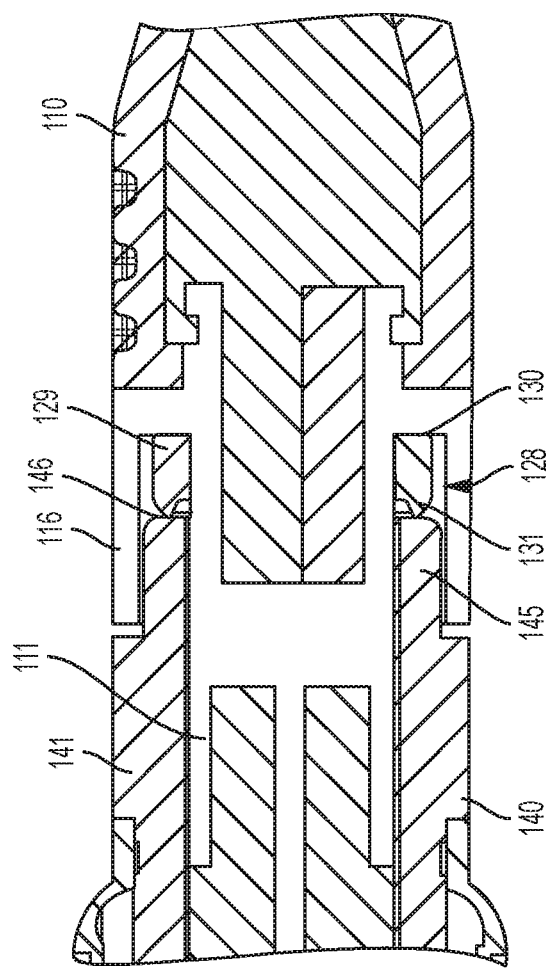
FIG. 8 is a cross-sectional view of the pair of the connectors of FIG. 7 prior to completing the mating engagement.
Figure 9:
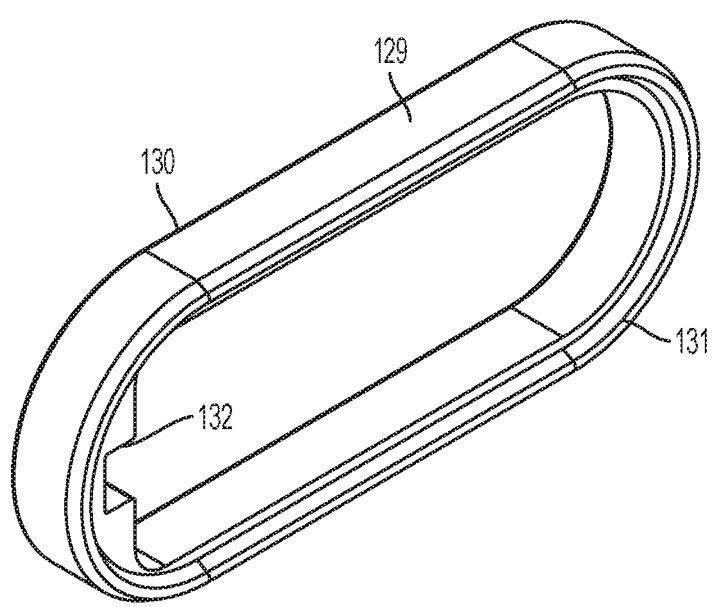
FIG. 9 is a perspective view of a sealing element of one of the connectors of the connector assembly of FIG. 3.

As shown in FIGS. 7-9, the sealing member 129 includes a flat side 130 configured to abut against an interior end wall of the annular space 128 and a shaped or protruding side 131. The sealing member 129 also includes a notch 132 that is shaped to surround the orientation alignment protrusion 118 on the side of the male connection portion 111.

As shown in FIGS. 3, 6A, 7, and 8, the female connection portion 141 of the second connector 140 includes a stepped portion 145 of reduced circumference or perimeter that is configured to fit within the annular space 128 of the first connector 110 when the mating engagement between the first connector 110 and the second connector 140 is formed. The stepped portion 145 defines a leading end 146 of the female connection portion 141. As the male connection portion 111 is slid into the female connection portion 141 to form the mating engagement, the stepped portion 145 of the female connection portion 141 becomes disposed within the annular space 128 of the male connection portion 111 to form an interlocking feature between the first and second connectors 110, 140. The leading end 146 of the female connection portion 141 comes into engagement with the shaped side 131 of the sealing member 129 to compress the shaped side 131 and cause the sealing member 129 to flex around the leading end 146 and seal the engagement between the first connector 110 and the second connector 140.

With reference to FIGS. 5B and 10B, the body 172 of the third connector 170 includes a skirt portion 176 surrounding the male connection portion 171 to define an annular space 188 between the skirt portion 176 and the male connection portion 171. A sealing member 189 is disposed within the annular space 188 for sealing the mating engagement between the third connector 170 and the fourth connector 200 to prevent moisture and environmental contaminants, such as dust, from entering the interiors of the mated third and fourth connectors 170, 200 and interfering with the electrical connections between the third and fourth connectors 170, 200. The sealing member 189 is similar to the sealing member 129 of the first connector 110, discussed above, but has dimensions corresponding to the configuration of the male connection portion 171 of the third connector 170.

As shown in FIGS. 3 and 6B, the female connection portion 201 of the fourth connector 200 includes a stepped portion 205 of reduced circumference or perimeter that is configured to fit within the annular space 188 of the third connector 170 when the mating engagement between the third connector 170 and the fourth connector 200 is formed. The stepped portion 205 defines a leading end 206 of the female connection portion 201. As the male connection portion 171 is slid into the female connection portion 201 to form the mating engagement, the stepped portion 205 of the female connection portion 201 becomes disposed within the annular space 188 of the male connection portion 171 to form an interlocking feature between the third and fourth connectors 170, 200. The leading end 206 of the female connection portion 201 comes into engagement with the sealing member 189 in the same manner as discussed above with respect to the first and second connectors 110, 140 to seal the engagement between the third connector 170 and the fourth connector 200.

According to a particular example of the present disclosure, the sealing members 129, 189 are made from a thermoplastic elastomer, such as a material consisting of fully cured ethylene propylene diene monomer (EPDM) rubber particles encapsulated in a polypropylene matrix.

Electrical Contact Features:

With reference to FIGS. 10A and 11A, according to one example of the present disclosure, the first connector 110 includes at least one electrical contact 124 disposed in the male connection portion 111 that is in electrical communication with the first electrode 10a so that continuous cardiac monitoring signals and cardiac treatment signals can be transmitted between the first connector 110 and the first electrode 10a. The at least one electrical contact 124 is configured to engage at least one corresponding electrical contact 154 in the second connector 140. The at least one corresponding electrical contact 154 in the second connector 140 is in electrical communication with the monitoring and treatment device 1 so that continuous cardiac monitoring signals and cardiac treatment signals can be transmitted between the second connector 140 and the ambulatory cardiac monitoring and treatment device 1.

According to one example of the present disclosure, the at least one electrical contact 124 is configured to transmit both a continuous cardiac monitoring signal, such as an ECG signal, from the first electrode 10a, and a cardiac treatment signal, such as a high voltage shock, to the first electrode 10a. The at least one corresponding electrical contact 154 in the second connector 140 is also configured to transmit both a continuous cardiac monitoring signal to the ambulatory cardiac monitoring and treatment device 1 and a cardiac treatment signal from the ambulatory cardiac monitoring and treatment device.

According to another example of the present disclosure, the first connector 110 includes a plurality of electrical contacts 123, 124 disposed in the male connection portion 111 and configured to engage corresponding electrical contacts 153, 154 in the female connection portion 141 of the second connector 140 when the mating engagement between the first and second connectors 110, 140 is formed. The plurality of electrical contacts 123, 124 in the first connector 110 includes at least one contact 123 configured to transmit a continuous cardiac monitoring signal, such as an ECG signal, from the first electrode 10a and at least one contact 124 configured to transmit a cardiac treatment signal, such as a high voltage shock, to the first electrode 10a. The corresponding electrical contacts 153, 154 of the second connector 140 include at least one contact 153 configured to transmit a continuous cardiac monitoring signal to the ambulatory cardiac monitoring and treatment device and at least one contact 154 configured to transmit a cardiac treatment signal from the ambulatory cardiac monitoring and treatment device.

According to another example of the present disclosure, the plurality of electrical contacts of the first connector 110 further includes a ground contact 125 disposed in the male connection portion 111. The second connector 140 includes a corresponding ground contact 155 that is engaged by the ground contact 125 of the first connector 110 when the mating engagement between the first and second connectors 110, 140 is formed.

According to a particular example of the present disclosure, as shown in FIGS. 7, 10A, and 11A, the first connector 110 includes a right to left arrangement of the patient monitoring contact 123 for transmitting the continuous cardiac monitoring signal, the patient treatment contact 124 for transmitting the cardiac treatment signal, and the ground contact 125 disposed within the male connection portion 111. The plurality of contacts 123, 124, 125 of the first connector 110 are formed as pins. The second connector 140 includes in a corresponding left to right arrangement of the continuous cardiac monitoring contact 153 for transmitting the continuous cardiac monitoring signal, the cardiac treatment contact 154 for transmitting the cardiac treatment signal, and the ground contact 155 disposed within the female connection portion 141. The plurality of contacts 153, 154, 155 of the second connector 140 are formed as sockets configured to receive the respective contact pins 123, 124, 125 of the first connector 110 to establish electrical communication between the respective contacts when the mating engagement between the first and second connectors 110, 140 is formed. Accordingly, when the mating engagement between the first and second connectors 110, 140 is formed, the continuous cardiac monitoring signal can be transmitted from the first electrode 10a to the ambulatory cardiac monitoring and treatment device 1 and the cardiac treatment signal can be transmitted from the ambulatory cardiac monitoring and treatment device 1 to the first electrode via the first and second connectors 110, 140.

As shown in FIGS. 10A and 11A, in accordance with the flattened profiles of the first and second connectors 110, 140, the plurality of contacts 123, 124, 125 of the first connector 110 are arranged in a common plane P1 extending parallel to the width of the first connector 110. The plurality of contacts 153, 154, 155 of the second connector 140 are also arranged within a common plane P2 extending parallel to the width of the second connector 140.

As shown in FIGS. 5A, 6A, 7, 10A, and 11A, the male connection portion 111 of the first connector 110 and the female connection portion 141 of the second connector 140 include additional interlocking features to establish and protect the electrical connections formed when the first and second connectors 110, 140 are in the mating engagement. In particular, the male connection portion 111 defines three hollow housings 120, 121, 122 surrounding each of the contact pins 123, 124, 125, respectively. Three solid housings 150, 151, 152 are formed as protrusions extending within the interior of the female connection portion 141 surrounding each of the contact sockets 153, 154, 155, respectively. When the mating engagement between the first and second connectors 110, 140 is formed, the solid housings 150, 151, 152 in the female connection portion 141 extend within respective hollow housings 120, 121, 122 defined in the male connection portion 111 to further close off and protect the contacts 123, 124, 125, 153, 154, 155. The solid housings 150, 151, 152 in the female connection portion 141 may have shapes corresponding to the shapes of the respective hollow housings 120, 121, 122 defined in the male connection portion 111 to provide for a positive engagement between the respective housings 120, 121, 122, 150, 151, 152 and thus consistent alignment between the corresponding electrical contacts 123, 124, 125, 153, 154, 155 during mating of the first and second connectors 110, 140.

As shown in FIGS. 10B and 11B, according to another particular example of the present disclosure, the electrical contacts in the third connector 170 and the fourth connector 200 are arranged in a similar manner to the electrical contacts in the first connector 110 and the second connector 140 discussed above.

The third connector 170 includes in a right to left arrangement two continuous cardiac monitoring contacts 182, 183 for transmitting continuous cardiac monitoring signals from the second electrode 10a, a cardiac treatment contact 184 for transmitting the cardiac treatment signal to the second electrode, and a ground contact 185. The contacts 182, 183, 184, 185 are each formed as pins disposed in the male connection portion 171. The fourth connector 200 includes in a corresponding left to right arrangement of two continuous cardiac monitoring contacts 212, 213 for transmitting continuous cardiac monitoring signals to the ambulatory cardiac monitoring and treatment device, a cardiac treatment contact 214 for transmitting a cardiac treatment signal from the ambulatory cardiac monitoring and treatment device 1, and a ground contact 215. The contacts 212, 213, 214, 215 are each formed as sockets disposed in the female connection portion 201, which are configured to receive the respective contact pins 182, 183, 184, 185 of the third connector 170 to establish electrical contact communication between the third and fourth connectors 170, 200 when the mating engagement is formed. Accordingly, when the mating engagement between the third and fourth connectors 170, 200 is formed, the patient monitoring signals can be transmitted from the second electrode 10b to the ambulatory cardiac monitoring and treatment device 1 and the patient treatment signal can be transmitted from the ambulatory cardiac monitoring and treatment device 1 to the second electrode 10b via the third and fourth connectors 170, 200.

As shown in FIGS. 10B and 11B, in accordance with the flattened profiles of the third and fourth connectors 170, 200, the plurality of contacts 182, 183, 184, 185 of the third connector 170 are arranged in a common plane extending parallel to the width of the third connector 170. The plurality of contacts 212, 213, 214, 215 of the fourth connector 200 are also arranged within a common plane extending parallel to the width of the fourth connector 200.

As shown in FIGS. 5B, 6B, 10B, and 11B, the male connection portion 171 of the third connector 170 and the female connection portion 201 of the fourth connector 200 include additional interlocking features to establish and protect the electrical connections formed when the third and fourth connectors 170, 200 are in the mating engagement. In particular, the male connection portion 171 defines three hollow housings 179, 180, 181 surrounding the contact pins 182, 183, 184, 185 with one hollow housing 179 surrounding both patient monitoring contacts 182, 183 and the other hollowing housings 180, 181 surrounding the patient treatment and ground contacts 184, 185, respectively. Three solid housings 209, 210, 211 are formed as protrusions extending within the interior of the female connection portion 201 surrounding each of the contact sockets 212, 213, 214, 215 with one solid housing 209 surrounding both patient monitoring contacts 212, 213 and the other solid housings 210, 211 surrounding the patient treatment and ground contacts 214, 215, respectively. When the mating engagement between the third and fourth 170, 200 connectors is formed, the solid housings 209, 210, 211 in the female connection portion 201 extend within respective hollow housings 179, 180, 181 defined in the male connection portion 171 to further close off and protect the contacts 182, 183, 184, 185, 212, 213, 214, 215. The solid housings 209, 210, 211 in the female connection portion 201 may have shapes corresponding to the shapes of the respective hollowing housings 179, 180, 181 defined in the male connection portion 171 to provide for a positive engagement between the respective housings 179, 180, 181, 209, 210, 211 and thus consistent alignment between the corresponding electrical contacts 182, 183, 184, 185, 212, 213, 214, 215 during mating of the third and fourth connectors 170, 200.

It is to be appreciated that the various contacts of the connectors 110, 140, 170, 200 may be of any type and number and may be placed in any arrangement within the connectors 110, 140, 170, 200 known to be suitable to those having ordinary skill in the art. For instance, the first connector 110 may include the left to right arrangement of a ground contact, a patient monitoring contact, a patient treatment contact, another patient monitoring contact, and another ground contact with the second connector 140 including a corresponding arrangement of contacts. The third connector 170 may include the left to right arrangement of a ground contact, two patient monitoring contacts, a patient treatment contact, two more patient monitoring contacts, and another ground contact with the fourth connector 200 including a corresponding arrangement of contacts.

According to a particular example of the present disclosure, the electrical contacts 123, 124, 125, 153, 154, 155, 182, 183, 184, 185, 212, 213, 214, 215 are made from a conductive metal material, such as beryllium copper. The contacts 123, 124, 125, 153, 154, 155, 182, 183, 184, 185, 212, 213, 214, 215 have a voltage rating of 2325 VDC and an energy of 150 J (35 A into 50 Ohm load, <9 ms). It is to be appreciated that the electrical contacts can be of any configuration, material, and specification known to be suitable to those having ordinary skill in the art for transmitting the patient monitoring signals and patient treatment signals described above.

Beneficial Features:

With reference to FIGS. 3-14, the connectors 110, 140, 170, 200 according to the above-discussed examples of the present disclosure offer a number of beneficial and advantageous features in comparison to other connectors known in the art.

Figure 12:
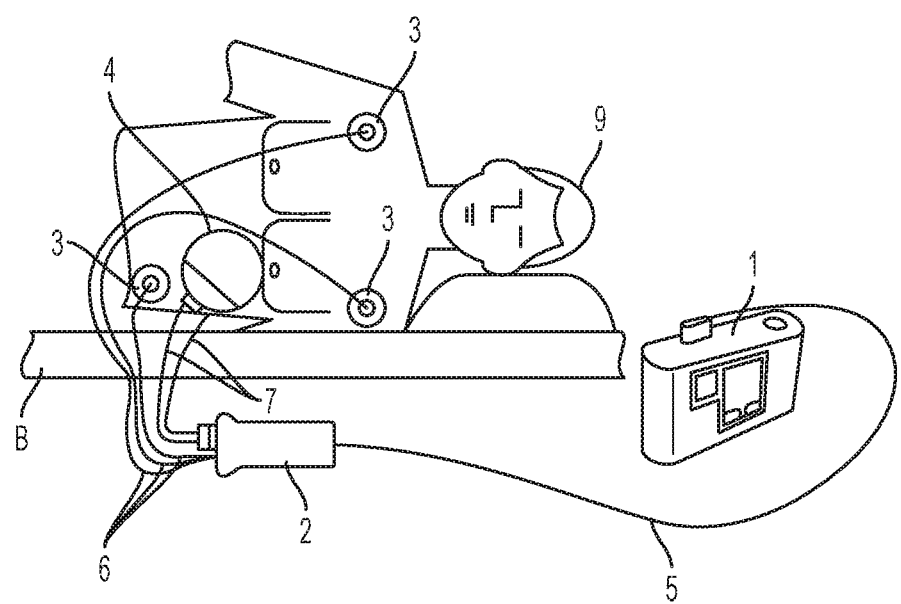
FIG. 12 is a schematic of a patient in a bed environment with the exemplary patient monitoring and treatment system shown in FIG. 1.

FIG. 12 illustrates schematic of a patient 9 wearing electrodes 3, 4 connected to a monitoring and treatment device 1 by way of a node 2 according to the example discussed above with reference to FIG. 1 while the patient 9 is lying on a bed B. As shown, the node 2 is relatively thick and bulky. As such, the node 2 can be a source of discomfort for the patient 9 should the node 2 become caught between the patient 9 and the bed B. The node 2 is also likely to become caught on the bed B or bed rails, on other furniture, or on doorways, hand rails, or other physical structures as the patient 9 moves, which creates a risk of an accidental disconnect between the electrodes 4 and the monitoring and treatment device 1 or injury to the patient. The node 2 may also be caught by the patient 9 during normal movement or by a nurse or other medical professional providing treatment to the patient 9. The node 2 also limits the patient's movement and may make it difficult for the patient 9 to dress and remove clothing.

Figure 13:
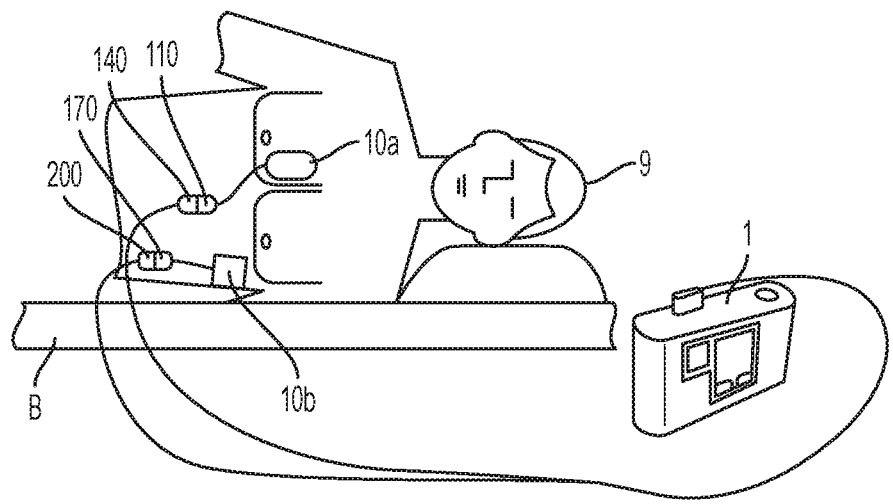
FIG. 13 is a schematic of a patient in a bed environment with a connector in accordance with an example of the present disclosure.

FIG. 13 illustrates a schematic of a patient 9 wearing electrodes 10a, 10b, which are separately connected to an ambulatory monitoring and treatment device 1 by way of the first and second connectors 110, 140 and the third and fourth connectors 170, 220 according to the above-discus discussed examples of the present disclosure while the patient 9 is lying on a bed B, in accordance with one example of the present disclosure. As shown in FIG. 13, the connectors 110, 140, 170, 200 have a flattened profile and a relatively smaller size when compared to node 2. As such, the connectors 110, 140, 170, 200 can be positioned relatively flat against the patient's body or more comfortably between the patient 9 and bed B. According to one example of the present disclosure, the connectors 110, 140, 170, 200 have a substantially oval or oblong circular shape defining the flattened profile with no sharp edges or corners and lie flat against the patient's body. The connectors 110, 140, 170, 200 are more comfortable to wear (e.g., relative to node 2) even if the connectors 110, 140, 170, 200 become caught between the patient 9 and the bed B. The connectors 110, 140, 170, 200 are also less likely (e.g., relative to node 2) to be caught on the bed B, other furniture, or other physical structures as the patient 9 moves. The connectors 110, 140, 170, 200 are also less likely (e.g., relative to node 2) to be caught by the patient 9 as the patient moves or by nurses or other medical personnel providing treatment to the patient 9. The connectors 110, 140, 170, 200 also limit interference with the patient's movement and with the patient's clothes as the patient 9 dresses or removes clothing. The smaller, flattened profile of the connectors 110, 140, 170, 200 when compared to, e.g., node 2, is in keeping of the use of the connectors 110, 140, 170, 200 and the electrodes 10a, 10b with the ambulatory cardiac monitoring and treatment device 1 that is intended to be portable and move with the patient 9 so that the patient 9 can move about while still being able to receive the beneficial monitoring and treatment provided by the device 1.

Figure 14:
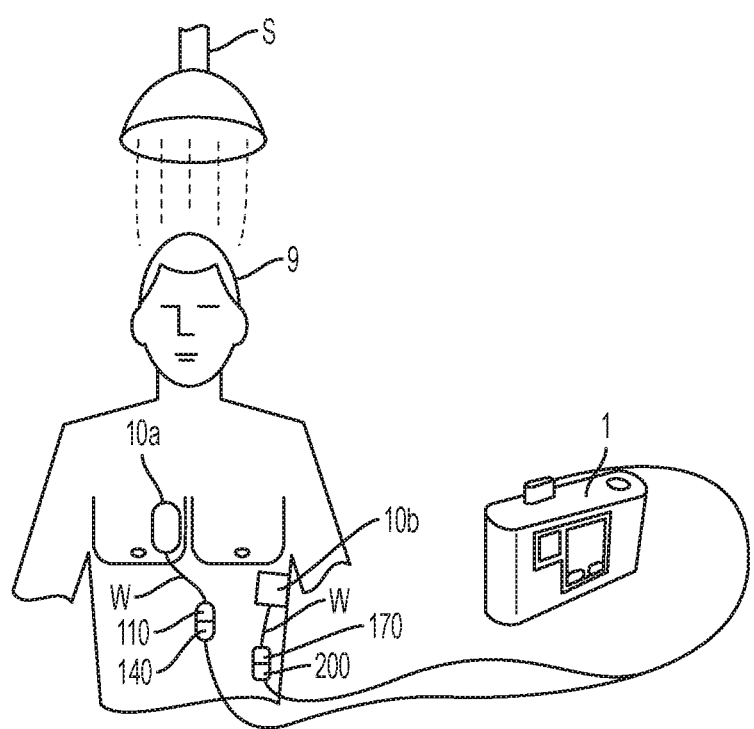
FIG. 14 is a schematic of a patient in a shower environment with a connector in accordance with an example of the present disclosure.

FIG. 14 illustrates a schematic of a patient 9 wearing electrodes 10a, 10b while in the shower S, in accordance with one example of the present disclosure. The connections between the first and second connectors 110, 140 and the third and fourth connectors 170, 200 are sealed and resistant to infiltration by water and debris. Accordingly, if desired, the patient 9 can use the shower S while remaining connected to and protected by the ambulatory cardiac monitoring and treatment device 1. Also, according to this example, the first and third electrodes 110, 170 may be disconnected from the second and fourth electrodes 140, 200 such that the electrodes 10a, 10b are disconnected from the ambulatory monitoring and treatment device 1 while the patient 9 uses the shower S. According to this example of the present disclosure, the wires W connecting the electrodes 10a, 10b to the first and third connectors 110, 170 can be configured to be short relative to the length of the patient's torso or the patient's height, e.g., 4-6 inches long, so that the patient may move about and bathe in the shower S with minimal interference. According another example, the wires W can be in the range of 6-12 inches long. According to another example, the wires W can be approximately 8 inches long. Further, as discussed above the first and third connectors 110, 170 are manufactured from suitable materials and sufficiently protect the electrical contacts 123, 124, 125, 182, 183, 184, 185 from water damage such that the connectors 110, 170 may be utilized even after being brought into the shower S.

Figure 15:
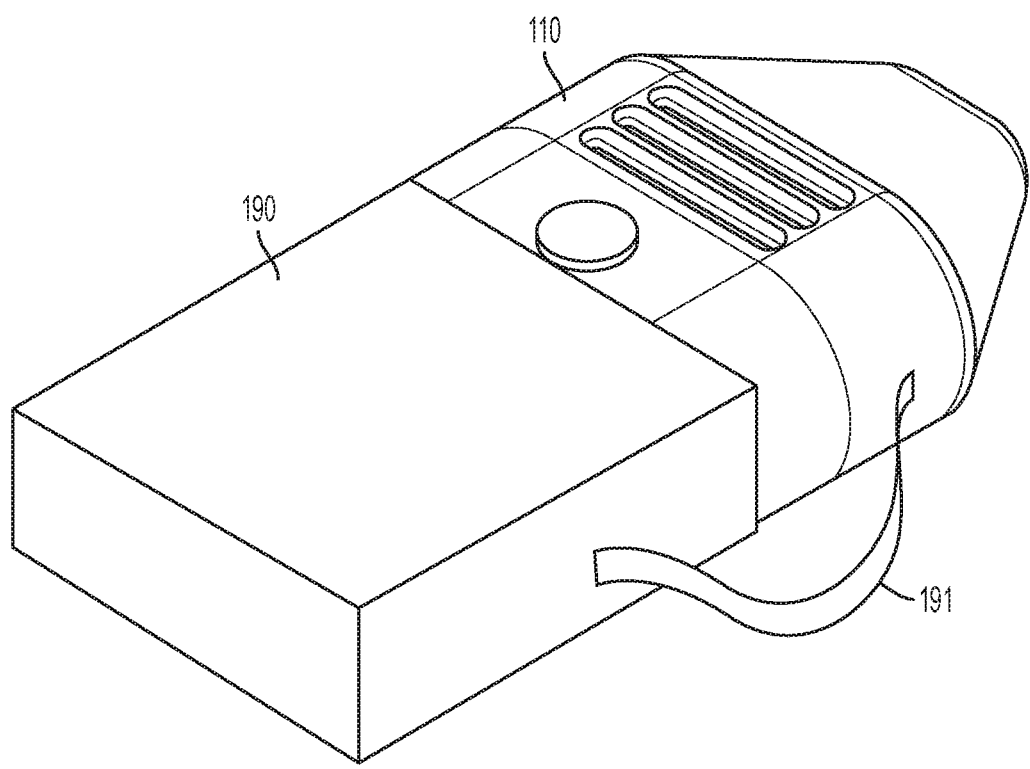
FIG. 15 is a perspective view of an exemplary embodiment of a connector having a cap disposed thereon.

According to the example of the disclosure shown in FIG. 15, the first connector 110 (as well as the third connector 170) may include a cap member 190 disposed thereon for protecting the interior of the first connector 110, including the contacts 123, 124, 125 from moisture, debris, and other contaminants when the first connector 110 is not connected to the second connector 140. The cap member 190 limits the amount of water that gets into the interior of the first connector 110 in the event the first connector 110 is brought into the shower S, as discussed above. The cap member 190 may be connected to the first connector 110 by a tether 191, which may be molded to the cap member 190 and/or the first connector 110, connected to the cap member 190 and/or the first connector 110 by an adhesive, or mechanically fastened or connected to the cap member 190 and/or the first connector 110.

Additionally, due to the smaller size and less material investment in the connectors 110, 140, 170, 200 (e.g., relative to node 2), the connectors 110, 140, 170, 200 are replaceable and may be disposed of in a cost-effective manner (e.g., relative to node 2).

According to one example of the present disclosure, the smaller size and flattened profile of the connectors 110, 140, 170, 200 is facilitated, at least in part, by utilizing two sets of smaller connectors 110, 140 & 170, 200, which are individually connected to separate electrodes 10a, 10b and to the ambulatory monitoring and treatment device 1. Because each set of connectors 110, 140 & 170, 200 does not need to relay monitoring signals and treatment signals for both electrodes 10a, 10b, the connectors 110, 140, 170, 200 can be made of a smaller size in comparison to other connectors known in the art. The smaller size and flattened profile of the connectors 110, 140, 170, 200 is also facilitated, at least in part, by arranging the contacts within the connectors 110, 140, 170, 200 in a single plane extending parallel to the width of the connector 110, 140, 170, 200. As shown in FIG. 10A, the contacts 123, 124, 125 of the first connector 110 are arranged along a common plane P1. As shown in FIG. 10B, the contacts 182, 183, 184, 185 of the third connector 170 are arranged along a common plane P3. As shown in FIG. 11A, the contacts 153, 154, 155 of the second connector 140 are arranged along a common plane P2. As shown in FIG. 11B, the contacts 212, 213, 214, 215 of the fourth connector 200 are arranged along a common plane P4.

As also discussed above with reference to FIGS. 3-14, the connectors 110, 140, 170, 200 incorporate numerous additional features that facilitate the use of two separate sets of connectors 110, 140 & 170, 200 by ensuring that the connectors 110, 140, 170, 200 cannot be mismatched when being connected to prevent improper connection and communications of the electrodes 10a, 10b with the ambulatory cardiac monitoring and treatment device 1. According to one example of the present disclosure, the male connection portion 111 of the first connector 110 has a thickness $t_1$ and width $w_1$ that corresponds to the thickness $t_2$ and width $t_2$ of the female connection portion 141 of the second connector 140, but not to the thickness $t_4$ and width $w_4$ of the female connection portion 201 of the fourth connector 200. In this manner, the first connector 110 can be mated with the second connector 140 but not with the fourth connector 200. Similarly, the male connection portion 171 of the third connector 170 has a thickness $t_3$ and width $w_3$ that corresponds to the thickness $t_4$ and width $w_4$ of the female connection portion 201 of the fourth connector 200, but not to the thickness $t_2$ and width $w_2$ of the female connection portion 141 of the second connector 140. In this manner, the third connector 170 can be mated with the fourth connector 200 but not with the second connector 140. The connectors 110, 140, 170, 200 may also include numerous indicators, such as the alignment indicators 117, 147, 177, 207 having different shapes and the connectors 110, 140, 170, 200 having different colors that assist the patient or the healthcare professional in distinguishing and correctly mating the connectors 110, 140, 170, 200.

According to one example of the present disclosure, the connectors 110, 140, 170, 200 also incorporate numerous orientation and alignment features to ensure that the connectors 110, 140, 170, 200 cannot be reverse connected with each other and to facilitate the connection between the first and second connectors 110, 140 and the third and fourth connectors 170, 200. The first connector 110 includes protrusions 118, 119 that align within slots 148, 149 defined in the second connector 140. The male connection portion 111 of the first connector 110 and the female connection portion 141 of the second connector 140 are also asymmetric in shape such that there is a fixed orientation of the first connector 110 and the second connector 140 with respect to each other in which the first and second connectors 110, 140 can be mated. The third connector 170 includes a protrusion 178 that aligns with a slot 208 defined in the fourth connector 200. The male connection portion 171 of the third connector 170 and the female connection portion 201 of the fourth connector 200 are also asymmetric in shape such that there is a fixed orientation of the third connector 170 and the fourth connector 140 with respect to each other in which the third and fourth connectors 170, 200 can be mated. The first connector 110 and the second connector 140 include corresponding alignment indicators 117, 147 that assist the patient or healthcare professional in determining that the first and second connectors 110, 140 are in the fixed orientation with respect to each other. The third connector 170 and the fourth connector 200 include corresponding alignment indicators 177, 207 that assist the patient or healthcare professional in determining that the third and fourth connectors 170, 200 are in the fixed orientation with respect to each other.

Additionally, according to one example of the disclosure, the connectors 110, 140, 170, 200 incorporate locking features that are configured to automatically engage when the connectors 110, 140, 170, 200 are mated with each other and provide a tactile and audible feedback that the locking features have become engaged so that the patient or healthcare professional can engage the locking features with each other by mating the connectors 110, 140, 170, 200 and be able to determine that the connectors 110, 140, 170, 200 are locked together in the mated engagement. The first connector 110 includes opposing flexible locking tabs 126, 127 that engage within corresponding retaining features 156, 157 defined in the second connector 200 when the first connector 110 is mated within the second connector 140. The locking tabs 126, 127 snap into the retaining features 156, 157 in a manner that can be felt by the patient or healthcare professional making the connection and that can be heard by producing on audible "click" noise. The third connector 170 and the fourth connector 200 incorporate the same locking features.

According to the one example, the locking features are also configured to limit inadvertent disengagement between the connectors 110, 140, 170, 200. For instance, the locking features may prevent the connectors 110, 140, 170, 200 from being disengaged by knocking, pressing, or bumping the connectors 110, 140, 170, 200. The locking tabs 126, 127 of the first connector 110 become positioned within the second connector 140 when the first and second connectors 110, 140 are mated so that the engagement between the locking tabs 126, 127 and the retaining features 156, 157 cannot be physically accessed other than through the release features of the second connector 140. The locking tabs 126, 127 and retaining features 156, 157 are also disposed opposite to each other so that actuation of release features on both sides of the connectors 110, 140 is required in order to disengage the locking features.

According one example of the disclosure, the second connector 140 and the fourth connector 200 also incorporate release features 158, 216 so that the locking features on the connectors 110, 140, 170, 200 can be disengaged without strain or substantial physical effort by the patient or healthcare professional. The second connector 140 incorporates buttons 159 embedded in a band 163 of soft, flexible material surrounding the second connector 140. The buttons 159 can be pressed inwardly from both sides of the second connector 140 simultaneously to cause the locking tabs 126, 127 on the first connector 110 to disengage from the retaining features 156, 157 on the second connector 140 and allow the male connection portion 111 of the first connector 110 to be withdrawn from the female connection portion 141 of the second connector 140. The release feature 216 on the fourth connector 200 is the same as the release feature 158 on the second connector 140.

Although a patient monitoring and treatment system and an electrode assembly for such a system have been described in detail for the purpose of illustration based on what is currently considered to be the most practical examples, it is to be understood that such detail is solely for that purpose and that the subject matter of this disclosure is not limited to the disclosed examples, but, on the contrary, is intended to cover modifications and equivalent arrangements. For example, it is to be understood that this disclosure contemplates that, to the extent possible, one or more features of any example can be combined with one or more features of any other example.

The invention claimed is:

1. An electrode assembly for patient monitoring and treatment, comprising:
   an electrode patch configured to be worn by a patient to provide extended and continuous monitoring of a cardiac function of the patient and delivery of an electrical cardiac treatment shock to the patient for treating a cardiac arrhythmia; and
   a first connector connected to the electrode patch and having a flattened profile, the first connector comprising:
   at least one electrical contact in electrical communication with the electrode patch to transmit a continuous cardiac monitoring signal from the electrode patch and to transmit the electrical cardiac treatment shock to the electrode patch for delivery to the patient,
   the at least one electrical contact configured to engage a corresponding electrical contact in a second connector for facilitating the extended and continuous monitoring of the cardiac function of the patient and delivery of the electrical cardiac treatment shock to the patient; and
   a male connection portion comprising at least one orientation aligning feature and at least two locking features disposed on outer surfaces, one on a top side and one on a bottom side,
   the at least one electrical contact being disposed in the male connection portion,
   wherein the first connector is configured to connect to the second connector, the second connector comprising a female connection portion, wherein the male connection portion of the first connector is configured to slide into the female connection portion of the second connector to form a mating engagement between the first connector and the second connector, and wherein the at least one orientation aligning feature is configured to engage the male connection portion of the first connector with the female connection portion of the second connector in a fixed orientation with respect to the second connector to form the mating engagement such that the at least one electrical contact of the first connector and the corresponding electrical contact of the second connector engage with each other,
   wherein, upon the male connection portion of the first connector sliding into the female connection portion of the second connector, the at least two locking features are configured to engage retaining features on a top side and a bottom side of an interior surface of the second connector to retain the first connector in the mating engagement, and
   wherein the at least two locking features are configured to be engaged simultaneously by a release mechanism on the second connector to release the first connector from the mating engagement, and
   wherein the release mechanism comprises two buttons, one disposed on a top side and another disposed on a bottom side of the exterior surface of the second connector, the two buttons being configured to disengage the at least two locking features from the retaining features when the two buttons are simultaneously pressed.

2. The electrode assembly according to claim 1, wherein the first connector further comprises a plurality of electrical contacts disposed in the male connection portion and configured to engage corresponding electrical contacts in the second connector when the mating engagement is formed, and
   wherein the plurality of electrical contacts comprises the at least one electrical contact in electrical communication with the electrode patch to transmit the continuous cardiac monitoring signal to the electrode patch and to transmit the electrical cardiac treatment shock to the electrode patch.

3. The electrode assembly according to claim 2, wherein the plurality of electrical contacts further comprises at least one ground contact.

4. The electrode assembly according to claim 2, wherein the at least one orientation aligning feature of the male connection portion is configured to engage the male connection portion of the first connector with the female connection portion of the second connector in the fixed orientation such that the plurality of electrical contacts of the first connector engage with corresponding electrical contacts of the second connector.

5. The electrode assembly according to claim 1, further comprising the second connector, the second connector being connected to a device for ambulatory cardiac monitoring and treatment,
   wherein the female connection portion is configured to be engaged by the male connection portion of the first connector to form the mating engagement.

6. The electrode assembly according to claim 5,
wherein the female connection portion of the second connector comprises the retaining features and
wherein the second connector further comprises the release mechanism configured to be actuated to simultaneously engage the at least two locking features to release the first connector and the second connector from the mating engagement.

7. The electrode assembly according to claim 6,
wherein each of the at least two locking features of the male connection portion comprises a flexible locking tab disposed on the male connection portion,
wherein the retaining features of the female connection portion comprise apertures extending through the top and bottom sides of the female connection portion, the apertures each being configured to receive a respective flexible locking tab, and
wherein each of the two buttons is disposed in a resiliently flexible material on a corresponding top and bottom side of the exterior surface of the second connector, each of the two buttons comprising a depending portion that extends into a respective aperture and is configured to contact a respective flexible locking tab on the male connection portion when the respective button is depressed to cause the respective flexible locking tab to disengage from the respective aperture.

8. The electrode assembly according to claim 1, wherein the flattened profile of the first connector allows for the first connector to be positioned relatively flat against a body of the patient and provide minimal interference with movement by the patient.

9. The electrode assembly according to claim 1, wherein the first connector comprises a substantially oval or oblong circular shape without any sharp edges or corners.

10. The electrode assembly according to claim 1, wherein the first connector has an overall width between 25-30 millimeters and an overall thickness between 11-16 millimeters.

* * * * *

UNITED STATES PATENT AND TRADEMARK OFFICE
CERTIFICATE OF CORRECTION

PATENT NO. : 10,632,301 B2
APPLICATION NO. : 15/282073
DATED : April 28, 2020
INVENTOR(S) : Christopher Joseph Desmarais It is certified that error appears in the above-identified patent and that said Letters Patent is hereby corrected as shown below:

In the Specification

Column 5, Line 61, delete "FIG.", insert -- FIG. 3. --
Column 16, Line 17, after "from" delete "an"
Column 19, Line 15, delete "in in", insert -- in --
Column 24, Line 11, delete "above-discus discussed", insert -- above-discussed --
Column 25, Line 60, delete "$t_2$ of", insert -- $w_2$ of --

Signed and Sealed this
Eighteenth Day of August, 2020

Andrei Iancu
*Director of the United States Patent and Trademark Office*